US011559548B2

United States Patent
Kaneko et al.

(10) Patent No.: US 11,559,548 B2
(45) Date of Patent: Jan. 24, 2023

(54) METHOD FOR PRODUCING HELPER T CELLS FROM PLURIPOTENT STEM CELLS

(71) Applicant: KYOTO UNIVERSITY, Kyoto (JP)

(72) Inventors: Shin Kaneko, Kyoto (JP); Norihiro Ueda, Kyoto (JP); Yasushi Uemura, Kashiwa (JP); Kyoko Fukuda, Kashiwa (JP)

(73) Assignee: KYOTO UNIVERSITY, Kyoto (JP)

( * ) Notice: Subject to any disclaimer, the term of this patent is extended or adjusted under 35 U.S.C. 154(b) by 425 days.

(21) Appl. No.: 16/494,265

(22) PCT Filed: Mar. 13, 2018

(86) PCT No.: PCT/JP2018/009661
§ 371 (c)(1),
(2) Date: Sep. 13, 2019

(87) PCT Pub. No.: WO2018/168829
PCT Pub. Date: Sep. 20, 2018

(65) Prior Publication Data
US 2020/0129551 A1    Apr. 30, 2020

(30) Foreign Application Priority Data
Mar. 14, 2017   (JP) .............................. JP2017-049244

(51) Int. Cl.
A61K 35/17 (2015.01)
C12N 5/0789 (2010.01)
C12N 15/86 (2006.01)
C12N 15/90 (2006.01)

(52) U.S. Cl.
CPC ............ A61K 35/17 (2013.01); C12N 5/0647 (2013.01); C12N 15/86 (2013.01); C12N 15/90 (2013.01); C12N 2501/125 (2013.01); C12N 2501/165 (2013.01); C12N 2501/2302 (2013.01); C12N 2501/2315 (2013.01); C12N 2501/26 (2013.01); C12N 2501/998 (2013.01); C12N 2501/999 (2013.01); C12N 2502/1394 (2013.01)

(58) Field of Classification Search
CPC ..................................................... A61K 35/17
See application file for complete search history.

(56) References Cited

U.S. PATENT DOCUMENTS

2013/0078226 A1    3/2013    Nakauchi
2018/0298337 A1    10/2018   Kaneko

FOREIGN PATENT DOCUMENTS

| EP | 2 853 590 A1 | 4/2015 |
| JP | 2016-136955 A | 8/2016 |
| WO | WO 2011/096482 A1 | 2/2011 |
| WO | WO 2011/096482 A1 | 8/2011 |
| WO | WO 2013/176197 | 11/2013 |
| WO | WO 2017/065288 A1 | 4/2017 |

OTHER PUBLICATIONS

Ghia et al. (Eur. J. Immunol. 2002. 32: 1403-1413) (Year: 2002).*
Ueda et al. (203. Lymphocytes, Lymphocyte Activation and Immunodeficiency, Including HIV and Other Infections: Poster III. Dec. 3, 2015. Blood (2015) 126 (23) : 3424. http://doi.org/10.1182/blood.V126.23.3424.3424). (Year: 2015).*
Coppernolle et al. (J Immunol 2009; 183:4859-4870; doi:10.4049/jimmunol.0900714). (Year: 2009).*
Smith et al. (Stem Cells. 2015;33:3174-3180 [published online Jul. 22, 2015]). (Year: 2015).*
Kirschmeier et al. (DNA 7(3):219-225 Apr. 1988 [published online Mar. 25, 2009 https://doi.org/10.1089/dna.1988.7.219]) (Year: 1988).*
Berner et al., Increased expression of CD40 ligand (CD154) on CD4+ T Cells as a Marker of Disease Activity in Rheumatoid Arthritis, Annals of Rheumatic Diseases, vol. 59, pp. 190-195, 2000.
Extended European Search Report dated Jan. 29, 2021 in European Application No. 18766784.5.
Schoenberger et al., T-Cell help for Cytotoxic T Lymphocytes is mediated by CD40-CD40L interactions, Nature, vol. 393, pp. 480-483, 1998.
Teitz-Tennenbaum et al., Radiotherapy combined with Intratumoral Dendritic Cell Vaccination Enhances the Therapeutic Efficacy of Adoptive T-Cell Transfer, Journal of Immunotherapy, vol. 32, No. 6, pp. 602-612, 2009.
Ballhausen, W. et al. Acquisition of an Additional Antigen Specificity After Mouse CD4 Gene Transfer into a T Helper Hybriddoma, J. Exp. Med, vol. 167, pp. 1493-1498, (1988).
Bulfone-Paus, .S. et al., Differential Regulation of Human T Lymphoblast Functions by IL-2 and IL-15, Cytokine, vol. 9, No. 7, pp. 507-513, (1997).
Cohen, G. et al., Isolation of Viable Antigen-Specific CD4 T Cells by CD40L Surface Trapping, Journal of Immunological Methods, vol. 302, pp. 103-115, (2005).
Dustin, M. Help to Go: T cells Transfer CD40L to Antigen-Pressing B Cells, Eur J. Immunol, vol. 47, pp. 31-34, (2017).
International Search Report and Written Opinion dated May 15, 2018 in Japanese Patent Application No. PCT/JP2018/009661.
Miro, F. et al. T Cell-Dependent Activation of Dendritic Cells Requires IL-2 and IFN-y Signaling in T Cells, J., Imunol, vol. 177, pp. 3625-3634, (2006).
Nishimura, T. et al., Generation of Rejuvenated Antigen-Specific T Cells by Reprogramming to Pluripotency and Redifferentiation, Cell Stem Cell, vol. 12, pp. 114-126, (2013).
Udea, et al., he 75th Annual Meeting of the Japanese Cancer Association, pp. 1412, (2016).
Udea, et al 3424 Generation of BCR-ABL Reactive CD4+ T Helper Cells By Programing and Redifferentiation. the 57th Annual Meeting and Exposition, (2015).

(Continued)

Primary Examiner — Scott Long
(74) Attorney, Agent, or Firm — Knobbe, Martens, Olson & Bear LLP

(57) ABSTRACT

A method of producing helper T cells, comprising:
(i) culturing T cells, which have been induced from pluripotent stem cells and into which a CD4 gene or a gene product thereof has been introduced, in a medium containing IL-2 and IL-15; and (ii) isolating CD40L-highly expressing T cells from cells obtained in step (i).

11 Claims, 7 Drawing Sheets
Specification includes a Sequence Listing.

(56) References Cited

OTHER PUBLICATIONS

Ballhausen, W., et al., Acquisition of an Additional Antigen Specificity After Mouse CD4 Gene Transfer into a T Helper Hybridoma, Journal of Experimental Medicine, vol. 167, pp. 1493-1498, 1988.

Dustin, M., Help to Go: T cells Transfer CD40L to Antigen-Presenting B Cells, European Journal of Immunology, vol. 47, pp. 31-34, 2017.

International Search Report and Written Opinion, dated Jun. 5, 2018, in Int'l Patent Application No. PCT/JP2018/009661.

Miro, F., et al., T Cell-Dependent Activation of Dendritic Cells Requires IL-12 and IFN-γ Signaling in T Cells, Journal of Immunology, vol. 177, pp. 3625-3634, 2006.

Ueda, N., et al., The 75th Annual Meeting of the Japanese Cancer Association, pp. 1412, 2016.

Ueda, N., et al., 3424 Generation of BCR-ABL Reactive CD4+ T Helper Cells By Reprograming and Redifferentiation, American Society of Hematology, 57$^{th}$ Annual Meeting and Exposition, 2015.

International Preliminary Report On Patentability, dated Sep. 26, 2019, in Int'l Patent Application No. PCT/JP2018/009661.

Notice of Reasons for Refusal dated Apr. 5, 2022 for JP Application 2019-506036.

\* cited by examiner

SEQUENCE LISTING

<160> NUMBER OF SEQ IDS NOS: 4

<210> SEQ ID NO 1
<211> LENGTH: 17
<212> TYPE: PRT
<213> ORGANISM: Artificial Sequence
<220> FEATURE:
<223> OTHER INFORMATION: b3a2

<400> SEQUENCE: 1

Ala Thr Gly Phe Lys Gln Ser Ser Lys Ala Leu Gln Arg Pro Val Ala
1               5                   10                  15

Ser

<210> SEQ ID NO 2
<211> LENGTH: 9
<212> TYPE: PRT
<213> ORGANISM: Artificial Sequence
<220> FEATURE:
<223> OTHER INFORMATION: WT1

<400> SEQUENCE: 2

Cys Tyr Thr Trp Asn Gln Met Asn Leu
1               5

<210> SEQ ID NO 3
<211> LENGTH: 458
<212> TYPE: PRT
<213> ORGANISM: Homo sapiens

<400> SEQUENCE: 3

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

```
Leu Ala Phe Thr Val Glu Lys Leu Thr Gly Ser Gly Glu Leu Trp Trp
225                 230                 235                 240

Gln Ala Glu Arg Ala Ser Ser Lys Ser Trp Ile Thr Phe Asp Leu
                245                 250                 255

Lys Asn Lys Glu Val Ser Val Lys Arg Val Thr Gln Asp Pro Lys Leu
                260                 265                 270

Gln Met Gly Lys Lys Leu Pro Leu His Leu Thr Leu Pro Gln Ala Leu
                275                 280                 285

Pro Gln Tyr Ala Gly Ser Gly Asn Leu Thr Leu Ala Leu Glu Ala Lys
                290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
                340                 345                 350

Lys Arg Glu Lys Ala Val Trp Val Leu Asn Pro Glu Ala Gly Met Trp
                355                 360                 365

Gln Cys Leu Leu Ser Asp Ser Gly Gln Val Leu Leu Glu Ser Asn Ile
                370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
                420                 425                 430

Ser Gln Ile Lys Arg Leu Leu Ser Glu Lys Lys Thr Cys Gln Cys Pro
                435                 440                 445

His Arg Phe Gln Lys Thr Cys Ser Pro Ile
                450                 455

<210> SEQ ID NO 4
<211> LENGTH: 19
<212> TYPE: PRT
<213> ORGANISM: Artificial Sequence
<220> FEATURE:
<223> OTHER INFORMATION: GAD65

<400> SEQUENCE: 4

Asp Val Met Asn Ile Leu Leu Gln Tyr Val Val Lys Ser Phe Asp Arg
1               5                   10                  15

Ser Thr Lys
```

METHOD FOR PRODUCING HELPER T CELLS FROM PLURIPOTENT STEM CELLS

PRIORITY AND CROSS REFERENCE TO RELATED APPLICATIONS

This application is the U.S. National Stage Application under 35 U.S.C. § 371 of International Application No. PCT/JP2018/009661, filed Mar. 13, 2018, designating the U.S. and published as WO 2018/168829 A1 on Sep. 20, 2018, which claims the benefit of Japanese Patent Application No. JP 2017-049244, filed Mar. 14, 2017. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled TOYA166025APCSEQLIST.txt, created and last saved on Sep. 13, 2019, which is 4,818 bytes in size. The information in the Electronic Sequence Listing is incorporated herein by reference in its entirety.

TECHNICAL FIELD

The present invention relates to a method of producing helper T cells from pluripotent stem cells, and a pharmaceutical comprising helper T cells produced from pluripotent stem cells.

BACKGROUND ART

Immune surveillance against tumors is established by cytotoxic T cells (CTLs), which are mainly composed of CD8-positive T cells that directly injure tumors, and helper T cells (Th cells), which are mainly composed of CD4-positive T cells and enhance the function of CTLs. On the other hand, dendritic cells (DCs) have a role as a control tower that controls the dynamics of other immune cells. Th cells are thought to be capable of producing an antitumor effect by activation of CTLs through activation of DCs.

If induction of tumor antigen-specific Th cells from pluripotent stem cells such as induced pluripotent stem (iPS) cells is possible, it may lead to development of a novel cellular immunotherapy based on administration of such cells into the living body for induction of a strong antitumor immune response. There has been a report on a method in which iPS cells (iPSCs) are prepared from antigen-specific CD8-positive CTLs, and the resulting cells are induced to differentiate again into CD8-positive CTSs (Non-patent Document 1 and Patent Document 1). In this method, since T-cell receptors (TCRs) of the CD8-positive CTLs are consistently taken over, the CD8-positive CTLs induced from the iPS cells exhibit the same antigen specificity as that of the original cells.

T-cell coreceptors (CD8 molecules in cases of CD8-positive CTLs, or CD4 molecules in cases of CD4-positive Th cells) effectively enhance the signals input into the cells upon recognition of antigens by TCRs, and this results in effective induction of antigen-specific immune reactions of the T cells. However, preparation of cells expressing CD4 molecules is difficult by the method described in Non-patent Document 1 although the method allows induction of cells expressing CD8 molecules. Thus, in cells induced from iPS cells derived from CD4-positive Th cells, exertion of sufficient helper function is impossible because of lack of CD4 molecules.

PRIOR ART DOCUMENTS

Patent Document

Patent Document 1: WO 2011/096482

Non-Patent Document

Non-patent Document 1: Nishimura T, et al., Cell Stem Cell. 12(1): 114-126, 2013

SUMMARY OF INVENTION

An object of the present invention is efficient production of CD4-positive Th cells from pluripotent stem cells. Another object of the present invention is to provide pharmaceuticals such as anticancer drugs using CD4-positive Th cells obtained by this method.

In order to achieve the above objects, the present inventors introduced a CD4 gene into T cells induced from pluripotent stem cells, and then the resulting CD4-positive T cells were cultured in a medium containing IL-2 and IL-15, and as a result discovered a cell population showing increased expression of CD40L. Further, the present inventors discovered that, by sorting and separation of a CD40L-positive cell population, Th cells which efficiently activate dendritic cells can be obtained, thereby completed the present invention.

That is, the present invention provides the following inventions.

[1] A method of producing helper T cells comprising:
 (i) culturing T cells, which have been induced from pluripotent stem cells and into which a CD4 gene or a gene product thereof has been introduced, in a medium containing IL-2 and IL-15; and
 (ii) isolating CD40L-highly expressing T cells from cells obtained in Step (i).
[2] The method according to [1], wherein the concentration of the IL-2 is 10 to 500 IU/ml, and the concentration of the IL-15 is 1 to 50 ng/ml.
[3] The method according to [1] or [2], wherein the T cells have been induced from the pluripotent stem cells by a method comprising:
 (1) inducing CD34-positive hematopoietic progenitor cells from pluripotent stem cells; and
 (2) culturing CD34-positive hematopoietic progenitor cells obtained in Step (1), in the presence of FLT3L (Flt 3 ligand) and IL-7.
[4] The method according to [3], wherein Step (1) comprises co-culturing pluripotent stem cells with C3H10T1/2, followed by co-culturing with C3H10T1/2 in the presence of VEGF, FLT3L, and SCF.
[5] The method according to [3] or [4], wherein Step (2) comprises co-culturing the CD34-positive hematopoietic progenitor cells with stromal cells.
[6] The method according to any one of [3] to [5], wherein said method of inducing the T cells from the pluripotent stem cells further comprises:
 (3) co-culturing cells obtained in Step (2), with peripheral blood mononuclear cells in the presence of IL-7 and IL-15.

[7] The method according to any one of [3] to [6], wherein said method of inducing T cells from the pluripotent stem cells further comprises:
bringing cells obtained in Step (2) into contact with mitogen, and/or
bringing cells obtained in Step (3) into contact with mitogen.

[8] The method according to any one of [1] to [7], wherein the CD4 gene has been introduced using a retrovirus vector.

[9] The method according to any one of [1] to [8], wherein the pluripotent stem cells are pluripotent stem cells having a rearranged TCR sequence of interest.

[10] The method according to [9], wherein the pluripotent stem cells are human iPS cells induced from lymphocytes that recognize a desired antigen(s).

[11] The method according to [10], wherein the lymphocytes that recognize a desired antigen(s) are lymphocytes that recognize BCR/ABL.

[12] A method of activating dendritic cells comprising:
bringing helper T cells containing CD4-positive CD40L-highly expressing T cells produced by the method according to any one of [1] to [11] into contact with isolated dendritic cells in vitro in the presence of an antigen(s).

[13] Helper T cells induced from pluripotent stem cells, the helper T cells comprising CD4-positive CD40L-highly expressing T cells.

[14] A pharmaceutical comprising the helper T cells according to [13].

[15] The pharmaceutical according to [14], further comprising dendritic cells.

[16] The pharmaceutical according to [14] or [15], further comprising an antigen.

[17] The pharmaceutical according to [16], wherein the antigen is a BCR/ABL fragment.

[18] The pharmaceutical according to any one of [14] to [17], which is a therapeutic agent for cancer.

According to the present invention, functional CD4-positive helper T cells can be produced by introducing a CD4 gene or a gene product thereof into T cells which have been induced from pluripotent stem cells, culturing the resulting cells in a medium containing IL-2 and IL-15, and then isolating CD40L-highly expressing cells. Further, according to the present invention, dendritic cells can be activated using the CD4-positive helper T cells. Thus, according to the present invention, CD4-positive helper T cells can be produced from pluripotent stem cells, and pharmaceuticals such as cancer therapeutic agents that contain CD4-positive helper T cells derived from pluripotent stem cells, which pharmaceuticals activate the immune function, can be provided.

DETAILED DESCRIPTION

Figure 1:
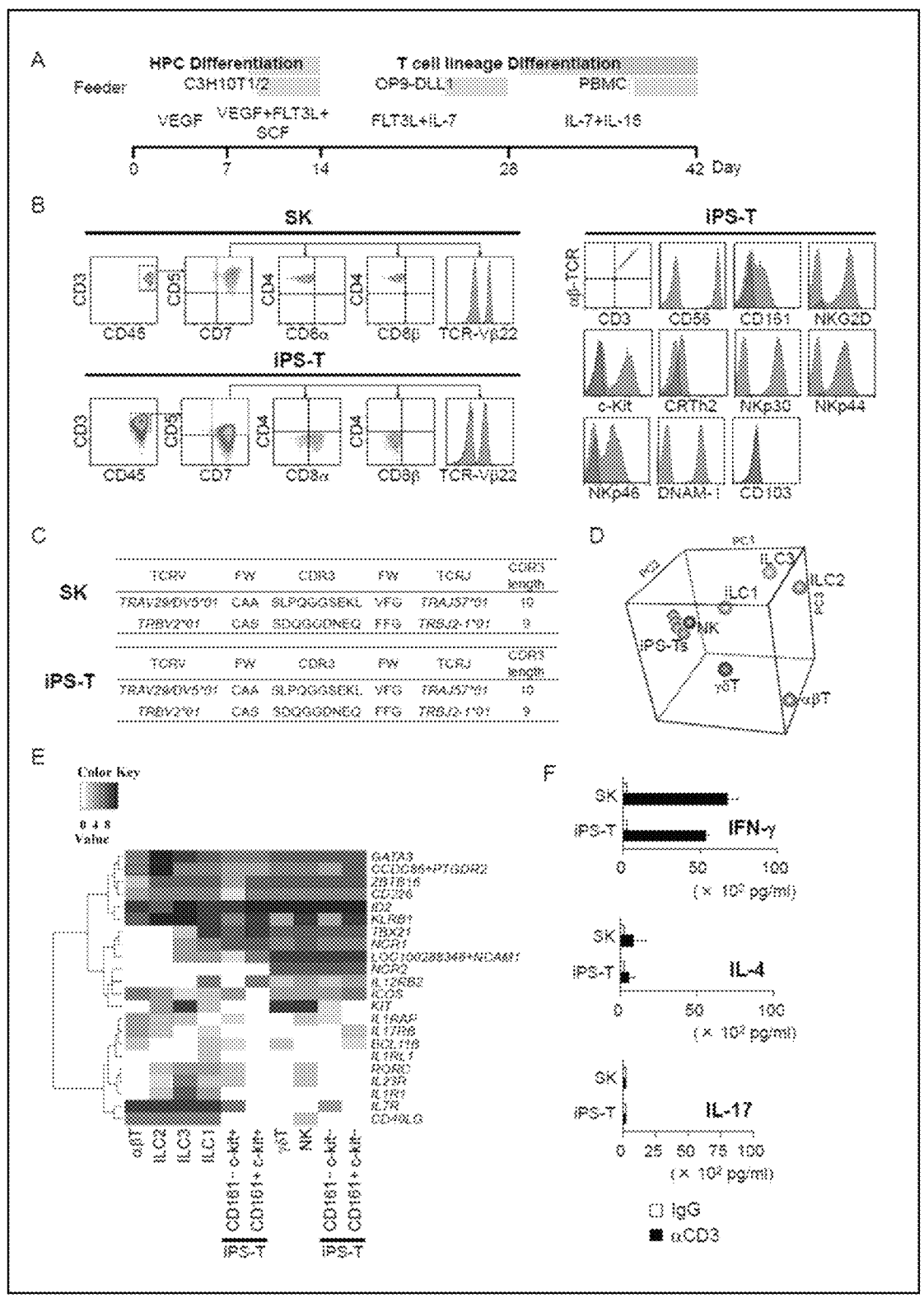
FIG. 1 is a diagram illustrating an experimental scheme and experimental results on re-differentiation of T-lineage cells from iPSCs derived from a CD4+ Th1 clone. (A) A culture protocol for the re-differentiation of the T-lineage cells from the iPSCs derived from the CD4+ Th clone. (B) Representative flow cytometry profiles of the indicated molecules on the original CD4+ Th clone (SK) and the regenerated T cells (iPS-T cells), which were observed 14 days after stimulation with phytohemagglutinin (PHA)-P. (C) Use of TCR genes and V-(D)-J junction region sequences in the original CD4+ Th1 clone (SK) and the iPS-T cells. (D) Principal component analysis of expression profiles of 146 kinds of selected T cells/ILC-associated genes. (E) Hierarchical clustering of expression of 22 kinds of selected genes associated with ILC subsets (halftone image). (F) Cytokine production. The original CD4+ Th1 clone (SK) and the iPS-T cells were stimulated with plate-bound control IgG or anti-CD3 monoclonal antibody (10 µg/ml) for 24 hours. The indicated cytokines in the culture supernatant were measured by ELISA. Each of the data shown is expressed as the average±SD for triplicate cultures, and the data represent results of three combinations of three independent experiments.

The method of producing CD4-positive helper T cells of the present invention comprises (i) culturing T cells, which have been induced from pluripotent stem cells and into which a CD4 gene or a gene product thereof has been introduced, in a medium containing IL-2 and IL-15; and (ii) isolating CD40L-highly expressing T cells from cells obtained in (i).

First, a description is given for the T cells which have been induced from pluripotent stem cells and into which a CD4 gene or a gene product thereof has been introduced.

Pluripotent Stem Cells

In the present invention, the pluripotent stem cells are stem cells having pluripotency that allows differentiation into many kinds of cells present in a living body, which stem cells also have the growth ability. The pluripotent stem cells at least include arbitrary cells which can be induced into the hematopoietic progenitor cells to be used in the present invention. Examples of the pluripotent stem cells include, but are not limited to, embryonic stem (ES) cells, embryonic stem cells derived from a cloned embryo obtained by nuclear transfer (ntES cells), germline stem cells ("GS cells"), embryonic germ cells ("EG cells"), induced pluripotent stem (iPS) cells, and pluripotent cells derived from cultured fibroblasts or bone marrow stem cells (Muse cells).

Methods for producing iPS cells are known in the art. These cells can be produced by introducing reprogramming factors into arbitrary somatic cells. Examples of the reprogramming factors herein include genes such as Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1, and gene products thereof. These reprogramming factors may be used individually, or may be used in combination. Examples of the combinations of the reprogramming factors include those described in WO 2007/069666; WO 2008/118820; WO 2009/007852; WO 2009/032194; WO 2009/058413; WO 2009/057831; WO 2009/075119; WO 2009/079007; WO 2009/091659; WO 2009/101084;

WO 2009/101407; WO 2009/102983; WO 2009/114949; WO 2009/117439; WO 2009/126250; WO 2009/126251; WO 2009/126655; WO 2009/157593; WO 2010/009015; WO 2010/033906; WO 2010/033920; WO 2010/042800; WO 2010/050626; WO 2010/056831; WO 2010/068955; WO 2010/098419; WO 2010/102267; WO 2010/111409; WO 2010/111422; WO 2010/115050; WO 2010/124290; WO 2010/147395; WO 2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat. Biotechnol. 26:1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat. Cell Biol. 11:197-203; R. L. Judson et al., (2009), Nat. Biotechnol., 27:459-461; Lyssiotis C A, et al. (2009), Proc Natl Acad Sci USA. 106:8912-8917; Kim J B, et al. (2009), Nature. 461:649-643; Ichida J K, et al. (2009), Cell Stem Cell. 5:491-503; Heng J C, et al. (2010), Cell Stem Cell. 6:167-74; Han J, et al. (2010), Nature. 463:1096-100; Mali P, et al. (2010), Stem Cells. 28:713-720; and Maekawa M, et al. (2011), Nature. 474:225-9.

Examples of the somatic cells include, but are not limited to, any of fetal somatic cells, neonatal somatic cells, and mature, healthy or diseased somatic cells, as well as any of primary cultured cells, subcultured cells, and established cell lines. Specific examples of the somatic cells include (1) tissue stem cells (somatic stem cells) such as neural stem cells, hematopoietic stem cells, mesenchymal stem cells, and dental pulp stem cells; (2) tissue progenitor cells; and (3) differentiated cells such as blood cells (peripheral blood cells, cord blood cells, and the like), lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells, and adipocytes.

For use in the purpose of production of CD4-positive T cells, iPS cells are preferably produced using, as somatic cells, lymphocytes (preferably T cells) that have undergone gene rearrangement of T-cell receptor (TCR). In cases where lymphocytes are used as the somatic cells, the reprogramming step is preferably carried out after activation of the lymphocytes by stimulation with an anti-CD3 antibody and an anti-CD28 antibody, or by stimulation with a desired antigen peptide(s), in the presence of interleukin-2 (IL-2). Such stimulation can be carried out by, for example, culturing the lymphocytes for a predetermined period in a medium supplemented with IL-2, the anti-CD3 antibody, and the anti-CD28 antibody. The anti-CD3 antibody and the anti-CD28 antibody may be those to which magnetic beads or the like are bound. Instead of adding these antibodies to the medium, the T cells may be stimulated by a certain period of culture on a culture dish having a surface to which the anti-CD3 antibody and the anti-CD28 antibody are bound. The stimulation may also be carried out by adding an antigen peptide(s) that can be recognized by human T cells to the medium. The antigen peptide means a peptide having a sequence of at least not less than nine amino acids constituting a desired antigen protein. Examples of such a peptide include peptides having a sequence composed of not less than 9 amino acids constituting the b3a2 subtype (which is also simply referred to as b3a2) of p210 of the BCR/ABL chimeric gene. Thus, by culturing lymphocytes in a medium supplemented with an antigen peptide, lymphocytes that recognize the antigen peptide can be selectively grown.

The CD4-positive T cells to be used in the present invention preferably has a desired antigen specificity. Thus, the lymphocytes to be used as the origin of the iPS cells preferably have a desired antigen specificity, and the lymphocytes may be specifically isolated by purification using an affinity column or the like to which the desired antigen is immobilized. This purification may also be carried out by employing a method in which lymphocytes having a desired antigen specificity are purified from a human tissue using a tetramer of MHC (major histocompatibility complex) (the so-called "MHC tetramer") to which the desired antigen is bound.

The mammalian individual from which the somatic cells are collected is not limited. The mammalian individual is preferably human. In cases where CD4-positive helper T cells prepared by the method of the present invention are used for blood transfusion, the somatic cells to be used as the origin of the iPS cells are preferably isolated from the subject for which the blood transfusion of the CD4-positive helper T cells is to be carried out, from the viewpoint of easily matching the type of the human leukocyte antigen (HLA) with that of the patient for which the blood transfusion is to be carried out.

Method of Induction of T Cells from Pluripotent Stem Cells

The method of induction of T cells from pluripotent stem cells may be carried out by a known method. Examples of the method include methods including the following Steps (1) and (2), preferably (1) to (3):

(Step 1) inducing CD34-positive hematopoietic progenitor cells from pluripotent stem cells;

(Step 2) culturing CD34-positive hematopoietic progenitor cells obtained in the Step (1), in the presence of FLT3L and IL-7; and (Step 3) co-culturing cells obtained in the Step (2), with peripheral blood mononuclear cells in the presence of IL-7 and IL-15.

The "T cells" means cells having TCRs on the cell surface, and the T cells may also have CD4 and CD8 on the cell surface. Thus, from the viewpoint of induction of T cells, only the (Step 1) and the (Step 2) are required. However, for efficiently increasing the content of T cells, the (Step 3) is preferably included.

(Step 1) Step of Inducing Hematopoietic Progenitor Cells from Pluripotent Stem Cells The hematopoietic progenitor cells are cells capable of differentiation into blood cells such as lymphocytes, eosinophils, neutrophils, basophils, erythrocytes, and megakaryocytes. They can be recognized based on, for example, the positivity of CD34, or the positivity of CD34 and CD43, which are surface antigens.

Examples of the method of inducing hematopoietic progenitor cells from pluripotent stem cells include a method in which pluripotent stem cells are co-cultured with C3H10T1/2, and then co-cultured with C3H10T1/2 in the presence of VEGF, FLT3L, and SCF, to obtain a net-like structure (which is also referred to as ES-sac or iPS-sac), followed by preparing hematopoietic progenitor cells therefrom. In this process, the culture may be carried out with addition of vitamin C. The "net-like structure" herein is a three-dimensional sac-shaped structure (in which a space is formed) derived from pluripotent stem cells. The structure is formed with an endothelial cell population and/or the like, and contains hematopoietic progenitor cells in the inside. Alternatively, the hematopoietic progenitor cells can be prepared from a net-like structure obtained by culturing pluripotent stem cells in the presence of VEGF on C3H10T1/2 according to a method described in Takayama N., et al. J Exp Med.

2817-2830 (2010). Other examples of the method of producing hematopoietic progenitor cells from pluripotent stem cells include a method based on formation of embryoid bodies and addition of cytokines (Chadwick et al. Blood 2003, 102: 906-15; Vijayaragavan et al. Cell Stem Cell 2009, 4: 248-62; Saeki et al. Stem Cells 2009, 27: 59-67), a method based on co-culture with stromal cells derived from a different species (Niwa A et al. J Cell Physiol. 2009 November; 221(2): 367-77), and a method based on combination of addition of cytokines and a coating agent (Matrigel or laminin fragment) (WO 2011/115308).

(Step 2) Step of Culturing Hematopoietic Progenitor Cells in Presence of FLT3L and IL-7

The medium to be used in Step 2 is not limited, and may be prepared by using, as a basal medium, a medium for animal cell culture, and adding FLT3L and IL-7 thereto. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and their mixed media. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines. Preferred examples of the basal medium in the Step 2 include aMEM medium supplemented with serum, L-glutamine, transferrin, and selenium.

The IL-7 concentration in the medium to be used in Step 2 is usually 0.1 ng/ml to 50 ng/ml, for example, 0.1 ng/ml, 0.2 ng/ml, 0.3 ng/ml, 0.4 ng/ml, 0.5 ng/ml, 0.6 ng/ml, 0.7 ng/ml, 0.8 ng/ml, 0.9 ng/ml, 1 ng/ml, 2 ng/ml, 3 ng/ml, 4 ng/ml, 5 ng/ml, 10 ng/ml, 20 ng/ml, 30 ng/ml, 40 ng/ml, or 50 ng/ml. The concentration is preferably 1 ng/ml.

The FLT3L concentration in the medium to be used in Step 2 is usually 1 ng/ml to 100 ng/ml, for example, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 50 ng/ml, or 100 ng/ml. The concentration is preferably 10 ng/ml.

An additive containing vitamin C, SCF, and TPO (thrombopoietin) may be further added to the medium to be used in Step 2.

The "vitamin C" means L-ascorbic acid and derivatives thereof, and "L-ascorbic acid derivative" means derivatives that become vitamin C by enzymatic reaction in the living body. Examples of the derivatives of L-ascorbic acid include vitamin C phosphate, ascorbic acid glucoside, ascorbyl ethyl, vitamin C ester, ascorbyl tetrahexyldecanoate, ascorbyl stearate, and ascorbyl 2-phosphate 6-palmitate. The vitamin C is preferably vitamin C phosphate. Examples of the vitamin C phosphate include L-ascorbic acid phosphate Na and L-ascorbic acid phosphate Mg. The vitamin C is preferably added separately every four days, every three days, every two days, or every day during the culture period. The vitamin C is more preferably added every day. The addition of the vitamin C to the medium is carried out usually in an amount corresponding to 5 ng/ml to 500 ng/ml. The amount is preferably an amount corresponding to 5 ng/ml, 10 ng/ml, 25 ng/ml, 50 ng/ml, 100 ng/ml, 200 ng/ml, 300 ng/ml, 400 ng/ml, or 500 ng/ml.

The concentration of the SCF to be used for the production of the hematopoietic progenitor cells in the medium is 10 ng/ml to 100 ng/ml, for example, 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 150 ng/ml, 200 ng/ml, or 500 ng/ml.

The concentration of the TPO to be used for the production of the hematopoietic progenitor cells in the medium is 10 ng/ml to 100 ng/ml, for example, 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 150 ng/ml, 200 ng/ml, or 500 ng/ml.

In Step (2), the hematopoietic progenitor cells may be cultured by adherent culture or suspension culture. In cases of adherent culture, a coated culture vessel may be used, and/or the hematopoietic progenitor cells may be co-cultured with feeder cells and/or the like. The feeder cells for the co-culture are preferably stromal cells. Specific examples of the stromal cells include cells of the bone-marrow stromal cell line OP9 (available from Riken BioResource Center). The OP9 cells may be preferably OP9-DL1 cells, which constantly express Delta-like 1 (Dll1) (Holmes R1 and Zuniga-Pflucker J C. Cold Spring Harb Protoc. 2009(2)). In cases where OP9 cells are used as the feeder cells, Dll1, or a fusion protein of Dll1 and Fc or the like, may be separately provided and added to the medium as appropriate. Examples of the Dl11 include proteins encoded by a gene having the nucleotide sequence of the NCBI accession No. NM_005618 in cases of human, or NM_007865 in cases of mouse; and naturally occurring mutants having a high sequence identity (for example, having a sequence identity of not less than 90%) to these proteins and having an equivalent function. The feeder cells are preferably replaced as appropriate during the culture. The replacement of the feeder cells may be carried out by transferring the subject cells, during their culture, onto feeder cells that are preliminarily plated. The replacement may be carried out every five days, every four days, every three days, or every two days.

In cases where the culture is carried out by suspension culture in Step 2, the cells are preferably cultured while being allowed to form aggregates (also referred to as spheres) in a state where the cells are not adhering to the culture vessel. The culture may be, but does not need to be, carried out using a culture vessel that has not been artificially treated for the purpose of enhancing adhesiveness to cells (for example, by coating treatment with an extracellular matrix or the like), or a culture vessel that has been subjected to coating treatment for artificially suppressing adhesion (for example, treatment with a polyhydroxyethylmethacrylate (poly-HEMA), a nonionic surfactant polyol (e.g., Pluronic F-127), or a phospholipid analogue (e.g., a water-soluble polymer containing 2-methacryloyloxyethyl phosphorylcholine as a constituent (Lipidure)). In cases where suspension culture is carried out in Step 2, the culture may be carried out with reference to Huijskens M J et al, J Leukoc Biol. 96: 1165-1175, 2014.

In cases where adherent culture is carried out in Step 2, the culture may be carried out using a culture vessel coated with an extracellular matrix. The coating treatment may be carried out by placing a solution containing the extracellular matrix in the culture vessel, and then removing the solution as appropriate. The extracellular matrix herein is a supramolecular structure present outside the cell, and may be either a naturally-occurring substance or an artificial (recombinant) substance. Examples of the extracellular matrix include substances such as polylysine, polyornithine, collagen, proteoglycan, fibronectin, hyaluronic acid, tenascin, entactin, elastin, fibrillin, and laminin, and fragments thereof. These extracellular matrices may be used in combination. For example, the extracellular matrix may be a product prepared from cells, such as BD Matrigel (trademark).

The temperature conditions for the culture of the hematopoietic progenitor cells in Step 2 are not limited. The temperature is, for example, about 37° C. to about 42° C., preferably about 37 to about 39° C. The culture period can be appropriately selected by those skilled in the art by monitoring of the number of cells and/or the like. Examples of the number of days include, but are not limited to, at least not less than 10 days, not less than 12 days, not less than 14 days, not less than 16 days, not less than 18 days, not less than 20 days, and not less than 21 days. The number of days is preferably 14 days.

The cells obtained in Step 2 may be stimulated with mitogen. The mitogen means a substance that promotes cell division of T cells, and examples of such a substance include pokeweed mitogen, anti-CD3 antibody, anti-CD28 antibody, phytohemagglutinin (PHA), concanavalin A (ConA), super antigens, and phorbol esters (including phorbol-12-myristate-13-acetate (PMA)).

(Step 3) Step of Co-culturing with Peripheral Blood Mononuclear Cells in Presence of IL-7 and IL-15

Step (3) is a step of isolating the cells obtained in the Step 2, and co-culturing the isolated cells with peripheral blood mononuclear cells.

The peripheral blood mononuclear cells to be used in Step 3 are preferably allogeneic to the pluripotent stem cells used in Step 1. Accordingly, in cases where human pluripotent stem cells are used, the peripheral blood mononuclear cells are preferably human peripheral blood mononuclear cells. The peripheral blood mononuclear cells are preferably subjected to a treatment for prevention of self-multiplication. Examples of such a treatment include irradiation and mitomycin treatment.

The medium to be used in Step 3 is not limited, and may be prepared by using, as a basal medium, a medium for animal cell culture, and adding IL-7 and IL-15 thereto. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and their mixed media. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines. Preferred examples of the basal medium in Step 2 include RPMI 1640 medium supplemented with serum and L-glutamine.

The IL-7 concentration in the medium to be used in Step 3 is 1 ng/ml to 100 ng/ml, for example, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 50 ng/ml, or 100 ng/ml. The concentration is preferably 10 ng/ml.

The IL-15 concentration in the medium to be used in Step 3 is 1 ng/ml to 100 ng/ml, for example, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 50 ng/ml, or 100 ng/ml. The concentration is preferably 10 ng to 20 ng/ml.

For the purpose of promoting the cell division of the T cells, mitogen may be further added for preparation of the medium. As the mitogen, those described above may be used.

The culture temperature conditions in the Step 3 are not limited. The temperature is, for example, about 37° C. to about 42° C., preferably about 37 to about 39° C. The culture period can be appropriately selected by those skilled in the art by monitoring of the number of cells and/or the like. Examples of the number of days include, but are not limited to, at least not less than 10 days, not less than 12 days, not less than 14 days, not less than 16 days, not less than 18 days, not less than 20 days, and not less than 21 days. The number of days is preferably 14 days.

Method for Introducing CD4 Gene or Gene Product

The method for introducing the CD4 gene or gene product into the T cells induced from pluripotent stem cells is not limited, and examples of the method include the following methods. In the present invention, examples of the gene product include RNAs and proteins. The CD4 gene is preferably a human gene, and examples of the gene include those encoding a protein which has the amino acid sequence of GenBank Accession No. AAH25782 (SEQ ID NO:3) or an amino acid sequence having an identity of not less than 80%, preferably not less than 90%, more preferably not less than 95% thereto, which protein is capable of activating dendritic cells when it is introduced into T cells.

In cases where the CD4 is introduced in the form of a gene (DNA), it may be introduced into pluripotent stem cells by a vector such as a virus, plasmid, or artificial chromosome vector using a method such as lipofection, liposome, or microinjection. Examples of the virus vector include retrovirus vectors, lentivirus vectors, adenovirus vectors, adeno-associated virus vectors, and Sendai virus vectors. Examples of the artificial chromosome vector include human artificial chromosomes (HACs), yeast artificial chromosomes (YACs), and bacterial artificial chromosomes (BACs and PACs). Examples of the plasmid which may be used include plasmids for mammalian cells. The vector may contain a regulatory sequence such as a promoter, enhancer, ribosome binding sequence, terminator, or polyadenylation site for allowing expression of the CD4 gene; and, if necessary, a sequence of a selection marker such as a drug resistance gene (e.g., kanamycin resistance gene, ampicillin resistance gene, or puromycin resistance gene), thymidine kinase gene, or diphtheria toxin gene; a gene sequence of a reporter such as a fluorescent protein, β-glucuronidase (GUS), or FLAG; or the like. Examples of the promoter include the SV40 promoter, LTR promoter, CMV (cytomegalovirus) promoter, RSV (Rous sarcoma virus) promoter, MoMuLV (Moloney mouse leukemia virus) LTR, HSV-TK (herpes simplex virus thymidine kinase) promoter, EF-α preomoter, CAG promoter, and TRE promoter (CMV minimal promoter having a Tet-responsive sequence containing seven consecutive tetO sequences). In cases where a TRE promoter is used, it is preferred to allow simultaneous expression of a fusion protein of tetR and VP16AD, or a fusion protein of reverse tetR (rtetR) and VP16AD in the same cells. Here, a vector having a TRE promoter and capable of expressing a fusion protein of reverse tetR (rtetR) and VP16AD is referred to as a drug-responsive induction vector. For incorporating an expression cassette composed of a promoter and a CD4 gene bound thereto into a chromosome of a pluripotent cell, and excising the expression cassette when necessary, the vector may have transposon sequences before and after this expression cassette. Examples of the transposon sequences include, but are not limited to, piggyBac. In another embodiment, for the purpose of removing the expression cassette, LoxP sequences may be placed before and after the expression cassette.

In cases where a drug-responsive induction vector is used, the introduction of the CD4 gene may be carried out for the pluripotent stem cells. In such cases, the CD4 gene can be expressed by addition of the corresponding drug to the medium. Thus, in cases where the drug-responsive induction vector is used, the addition of the corresponding drug to the medium can be regarded as the introduction of the CD4 gene. Examples of the corresponding drug include doxycycline. In cases where a vector having LoxP sequences is used, for example, the expression may be stopped by introduction of Cre into the cells after a desired period of time.

In cases where the CD4 is introduced in the form of an RNA, it may be introduced into the pluripotent stem cells by a method such as electroporation, lipofection, or microinjection.

In cases where the CD4 is introduced in the form of a protein, it may be introduced into the pluripotent stem cells by a method such as lipofection, fusion with a cell membrane-permeable peptide (e.g., HIV-derived TAT or polyarginine), or microinjection.

In cases where the CD4 is introduced in the form of such a gene product, since the half-life of the gene product is short, the introduction may be carried out a plurality of times. The number of times of the introduction may be calculated as appropriate taking into account the period during which expression of the CD4 gene is required, and referring to the half-life. Examples of the number of times of the introduction include three times, four times, five times, six times, and a larger number of times.

Step of Culturing CD4-Positive T Cells in Medium Containing IL-2 and IL-15

The medium to be used in this step is not limited, and may be prepared by using, as a basal medium, a medium for animal cell culture, and adding IL-2 and IL-15 thereto. Examples of the basal medium include Iscove's Modified Dulbecco's Medium (IMDM), Medium 199, Eagle's Minimum Essential Medium (EMEM), aMEM medium, Dulbecco's modified Eagle's Medium (DMEM), Ham's F12 medium, RPMI 1640 medium, Fischer's medium, and Neurobasal Medium (Life Technologies), and their mixed media. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines. Preferred examples of the basal medium in this step include aMEM medium supplemented with serum, L-glutamine, transferrin, and selenium.

The IL-2 concentration in the medium is usually 10 IU/ml to 500 IU/ml, for example, 10 IU/ml, 20 IU/ml, 30 IU/ml, 40 IU/ml, 50 IU/ml, 60 IU/ml, 70 IU/ml, 80 IU/ml, 90 IU/ml, 100 IU/ml, 150 IU/ml, 200 IU/ml, 250 IU/ml, 300 IU/ml, 350 IU/ml, 400 IU/ml, 450 IU/ml, or 500 IU/ml. The IL-2 concentration is preferably 100 IU/ml.

The IL-15 concentration in the medium is usually 1 ng/ml to 50 ng/ml, for example, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 25 ng/ml, or 50 ng/ml. The concentration is preferably 5 ng/ml.

In this step, the CD4-positive T cells may be subjected to either adherent culture or suspension culture. Suspension culture is preferred.

The culture temperature conditions for the culture of the CD4-positive T cells are not limited. The temperature is, for example, about 37° C. to about 42° C., preferably about 37 to about 39° C. The culture period can be appropriately selected by those skilled in the art by monitoring of the number of cells and/or the like. The number of days is not limited. For example, it is at least not less than about 1 day, not less than about 2 days, or not less than about 3 days, and not more than about 5 days.

Step of Isolating CD40L-Highly Expressing T Cells

The T cells obtained by culturing the CD4-positive T cells in the medium containing IL-2 and IL-15 are subjected to sorting based on the expression level of CD40L, to obtain CD40L-highly expressing T cells (CD40L$^{high}$ CD4$^+$ iPS-T cells). The "CD40L-highly expressing T cells" means T cells expressing CD40L at a level higher than a predetermined level. Examples of such cells include T cells expressing CD40L at an expression level higher than a level at which detection is possible with an anti-CD40L antibody, and T cells expressing CD40L at a level higher than the expression level in negative control cells (for example, Fluorescence Minus One (FMO) Control), or, when the negative control cells show large variation of the expression level, T cells expressing CD40L at a level higher than the highest expression level in the negative control cells. The CD40L-highly expressing T cells can be isolated (purified) using an anti-CD40L antibody.

The purification of the CD40L-positive cells may be carried out by a method well known to those skilled in the art, and the method is not limited. The method may be carried out using a CD40L antibody supported on magnetic beads, or by flow cytometry using a CD40L antibody.

The CD40L-highly expressing T cells obtained may be stimulated with mitogen or the like. Examples of the mitogen include pokeweed mitogen, anti-CD3 antibody, anti-CD28 antibody, and phytohemagglutinin (PHA).

Method of Activating Dendritic Cells

By bringing CD4-positive helper T cells produced by the above-described method into contact with dendritic cells in vitro in the presence of antigen, the dendritic cells can be activated.

The dendritic cells are cells having a function by which an antigen can be incorporated and bound to an MHC molecule for presentation of the antigen. Since the dendritic cells can be activated by contacting with CD4-positive helper T cells produced by the method of the present invention, the dendritic cells may be immature dendritic cells.

The "activation of dendritic cells" means acquisition of a function by which antigen-specific T cells can be activated, more preferably means acquisition of a function by which antigen-specific CD8-positive T cells can be activated. The activation can also be carried out by confirmation of expression of CD83 or CD86. The activation of dendritic cells is, in other words, maturation of immature dendritic cells into mature dendritic cells.

Preferably, the dendritic cells are dendritic cells isolated from a donor by a blood component separator and density gradient centrifugation, and have the same MHC molecules as those of the CD4-positive helper T cells.

The antigen to be used in the activation of the dendritic cells is a peptide having a sequence of at least nine consecutive amino acids in a protein specifically recognized by the CD4-positive helper T cells produced by the method of the present invention. For example, in cases where the CD4-positive T cells have a TCR that specifically recognize b3a2 peptide, the b3a2 peptide is used as the antigen.

The b3a2 peptide is a part of the protein encoded by the b3a2-type BCR/ABL chimeric gene, and has a sequence of at least nine consecutive amino acids that can be contained in the peptide binding cleft of HLA-class II molecules. The b3a2-type BCR/ABL chimeric gene means a fusion gene of BCR and ABL, containing the B3 exon from the M-BCR portion of BCR, and the A2 exon from ABL.

The medium to be used for the activation of the dendritic cells may be a medium for animal cell culture. Examples of the basal medium include Iscove's Modified Dulbecco's Medium (IMDM), Medium 199, Eagle's Minimum Essential Medium (EMEM), aMEM medium, Dulbecco's modified Eagle's Medium (DMEM), Ham's F12 medium, RPMI 1640 medium, Fischer's medium, and Neurobasal Medium (Life Technologies), and their mixed media. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines.

The length of time required for the activation of the dendritic cells is not limited, and may be several hours. Examples of the length of time include 2 hours, 3 hours, 4 hours, 5 hours, 6 hours, 12 hours, and 24 hours. The length of time is preferably 5 hours.

Pharmaceuticals

The present invention provides a pharmaceutical such as a cancer therapeutic agent containing: CD4-positive helper T cells produced by the method described above (helper T cells induced from pluripotent stem cells, which helper T cells are composed of CD4-positive CD40L-highly expressing T cells); and/or dendritic cells activated by the method described above; and/or an antigen peptide.

In cases where the pharmaceutical is a cancer therapeutic agent containing CD4-positive helper T cells, the cancer to be treated is preferably cancer cells expressing, in the cancer cells, an antigen specifically recognized by the CD4-positive T cells. For example, in cases where the CD4-positive helper T cells have a TCR that specifically recognizes b3a2, the cancer to be treated is cancer cells expressing b3a2, that is, leukemia caused by a chromosome having a BCR/ABL chimeric gene (Philadelphia chromosome).

The dendritic cells activated by the CD4-positive helper T cells are also capable of activating lymphocytes (for example, CD8-positive T cells) that recognize an antigen other than the antigen recognized by the CD4-positive helper T cells, when the other antigen is presented. Thus, the cancer to be treated by the cancer therapeutic agent containing dendritic cells is not limited.

In cases where the therapeutic agent contains dendritic cells, the activated dendritic cells may be used as they are as the therapeutic agent. In cancer treatment, dendritic cells may be made to present a tumor antigen by a method such as mixing with a cell lysate of cancer cells, contacting with a peptide, or introduction of a tumor antigen gene, to provide the antigen-presenting dendritic cells as the cancer therapeutic agent.

Examples of the method for administration of the cancer therapeutic agent to a patient include a method in which the produced CD4-positive helper T cells, and/or the dendritic cells activated by the method described above, are suspended in physiological saline or the like, and the resulting suspension is directly transplanted to a muscle tissue of the patient, and a method in which the dendritic cells are suspended in physiological saline or the like, and the resulting suspension is intravenously injected.

EXAMPLES

The present invention is described below more concretely by way of Examples. However, the scope of the present invention is not limited to these Examples.

Materials and Methods

Peptides, Cytokines, and Compounds

HLA-DR9 (DRB1*09:01)-restricted b3a2 type BCR-ABL junction peptide (ATGFKQSSKALQRPVAS: SEQ ID NO:1)

HLA-A24 (A*24:02)-restricted modified Wilms tumor 1(WT1)$_{235-243}$ epitope peptide (CYTWNQMNL: SEQ ID NO:2)

HLA-DR53 (DRB4*01:03)-restricted glutamic acid decarboxylase 65 (GAD65)$_{113-131}$ peptide (DVMNILLQYVVKSFDRSTK: SEQ ID NO:4)

In the modified WT1$_{235-243}$ peptide, M at the amino acid position 2 of the wild-type WT1$_{235-243}$ peptide was substituted with Y (CYTWNQMNL: SEQ ID NO:2).

Recombinant human (rh)-type IL-2, rh-type IL-4, and rh-type granulocyte-macrophage colony-stimulating factor (GM-CSF) (Primmune)

rh-type IL-7, rh-type IL-15, and rh-type FMS-like tyrosine kinase 3 ligand (FLT3L) (Peprotec)

rh-type basic fibroblast growth factor (bFGF) and phytohemagglutinin-P (PHA-P) (Wako Pure Chemical Industries, Ltd.)

rh-type vascular endothelial growth factor (VEGF) and rh-type stem cell factor (SCF) (R&D systems)

Penicillin-killed Streptococcus pyogenes (OK432) (Chugai Pharmaceutical Co., Ltd.)

Cells

Peripheral blood mononuclear cells (PBMCs) isolated from healthy donors were used (Eur J Immunol 38:1012-1023., 2008). Human monocyte-derived dendritic cells (DCs) were induced according to the description in J Immunol 183:201-208., 2009. Commercially available products of the human CML cell line K562, the human myeloid leukemia cell line THP-1, and the human lung cancer cell line PC9 were used. Mouse L fibroblasts transfected with the HLA class II gene were used (Hum Immunol 59:549-560.1998). For use of cells isolated from healthy adults, informed consent was obtained from all donors. All studies were carried out in accordance with Declaration of Helsinki, and with appropriate approval by the ethical committee of each facility.

Preparation of iPSCs from HLA Class II-Restricted Antigen-Specific CD4$^+$ T Cell Clones According to the description in Cell Stem Cell 12: 114-126. 2013, transduction with reprogramming factors was carried out by the Sendai virus system using pSeV [KOSM302L] (obtained from Dr. Nakanishi, National Institute of Advanced Industrial Science and Technology (AIST)), to perform reprogramming of an HLA-DR9-restricted b3a2-specific CD4$^+$ Th1 clone (SK) (Ueda N, Cell Mol Immunol.2016) and an HLA-DR53-restricted GAD35$_{113-131}$ peptide-specific CD4$^+$ Th clone (SA32.5) (Hum Immunol 59:549-560.1998) to iPSCs. These iPSC clones were negative for the residual transgene, showed pluripotency characterized by expression of pluripotency-associated molecules and teratoma formation in immunodeficient mice, and had the normal karyotype (not shown in the figures).

T Cell Differentiation from iPSCs

The iPSCs were allowed to differentiate into T cells by the method described in Cell Stem Cell. 12(1):114-126, 2013. More specifically, iPSC clusters were transferred onto C3H10T1/2 feeder cells, and cultured in EB (embryoid body) medium containing rh-type VEGF. On Day 7, rh-type SCF and rh-type FLT3L were added. On Day 14, hematopoietic progenitor cells were collected, and then transferred onto OP9-DL1 cells, followed by performing co-culture in OP9 medium in which rh-type IL-7 and rh-type FLT3L are present. On Day 35, using allogeneic PBMCs as antigen-presenting cells (APCs), T cells were stimulated with PHA-P in the presence of rh-type IL-7 (10 ng/ml) and rh-type IL-15 (10 ng/ml) at 14-day intervals.

Antibodies Used for Flow Cytometry and Functional Assay

HLA-A*24:02/WT1235-243 tetramer was used for detection of WT1 peptide-specific cytotoxic T lymphocytes (CTLs), and HLA-A*24:02/HIVEnv584-592 tetramer was used as a negative control. Using a FACSCalibur flow cytometer and a FACSAria II flow cytometer (BD Biosciences), stained cell samples were analyzed, and data were processed using the FlowJo software program (Tree Star, Ashland, Oreg., USA). The relative fluorescence intensity (RFI) was calculated as the ratio of the mean fluorescence intensity (MFI) of a particular marker to the MFI of an isotype control.

Transfectants cDNA encoding HLA-DR9 (DRB1*09:01) has so far been described (Ueda N, Cell Mol Immunol. 2016). cDNA encoding BCR-ABL p210 was purchased from Addgene (Cambridge, Mass., USA). cDNA encoding BCR-ABL p210, HLA-A24(A*24:02), HLA-DRA, or HLA-DR9, or a minigene encoding the HLA-A24-restricted modified WT1235-243 epitope was inserted into the lentivirus vector CSII-EF-MCS (RIKEN BioResource Center, Tsukuba, Japan). Lentiviral transduction was carried out according to the description in Zhang, R., Cancer Immunol Res 2015. The lentivirus vector for expression of HLA-A*24:02 and the lentivirus vector for expression of the minigene encoding the modified WT1235-243 epitope were transduced into the luciferase gene-expressing K562 line (K562-Luc) (K562-Luc-A24-WT1 minigene cells). The lentivirus vectors for expression of HLA-DRA*01:01 and HLA-DRB1*09:01 and/or BCR-ABL p200 were transduced into the THP-1 line (THP-1-DR9 cells, THP1-DR9-BCRABL cells).

Functional Assay of T Cells

Cell proliferation was evaluated by [$^3$H]-thymidine incorporation assay. Cytotoxic activity was measured using $^{51}$Cr release assay. The cytokine levels in the culture supernatant were evaluated by enzyme-linked immunosorbent assay (ELISA; hIFN-γ: eBiosciences) or bead-based multiplex immunoassay (BD Cytometric Bead Array; BD Biosciences).

Analysis of T-Cell Antigen Receptor (TCR) Gene Rearrangement in T-Cell Clones

The V segment, D segment, and J segment of rearranged TCR-α-chain and TCR-β chain of T cells or iPS-T cells were identified according to the description in J Immunol 170: 947-960.2003. The segment nomenclature used was in accordance with the conventional method by ImMunoGeneTics (IMGT). These V segment, D segment, and J segment were identified by comparison of the obtained sequences against the IMGT database (http://www.imgt.org/) using an online tool (IMGT/V-QUEST).

Real-time PCR

Using an RNeasy Micro kit (Qiagen, Valencia, Calif.), total RNA was extracted from iPSCs. Together with 6-mer random primers, a high-capacity cDNA reverse-transcription kit (Applied Biosystems, Foster City, Calif., USA) was used to synthesize cDNA, and then RT-PCR was carried out using ExTaq HS (Takara, Shiga, Japan), followed by performing quantitative PCR using a TaqMan Array Human Stem Cell Pluripotency Card (Applied Biosystems). Each PCR reaction was standardized against 18S rRNA.

RNA Sequencing cDNA was synthesized using a SMARTer Ultra Low Input RNA kit for Illumina Sequencing HV (Clontech, Mountain View, Calif., USA), and then Illumina libraries were prepared using a Low Input Library Prep kit (Clontech). Under the 101 cycle single-read mode, sequencing of the libraries was carried out using HiSeq 2500. All sequence reads were extracted in the FASTQ format using BCL2FASTQ conversion software 1.8.4 in the CASAVA 1.8.2 pipeline. Using TopHat v2.0.8b, these sequence reads were mapped against the hg19 reference genome downloaded on Dec. 10, 2012, and the sequence reads were quantified using RPKM for Genes. The data are deposited in NCBI Gene Expression Omnibus (http://www.ncbi.nlm.nih.gov/geo/, Accession No. GSE94332). Subpopulations of iPS-T cells were obtained based on expression of CD161 and c-Kit, and gene expression profiles of these subpopulations were compared against those of NK cells, ILC1s, ILC2s, ILC3s, αβ-T cells, and γδ-T cells. The NK cells, TLC1s, ILC2s, ILC3s, αβ-T cells, and γδ-T cells were separated from PBMCs of healthy donors. For pathway analysis, the fold change in the average expression level was calculated to reveal differentially expressed genes (|log 2FC|>1). Using org.Hs.eg.db 3.2.3 of the data analysis software R version 3.2.2, a hypergeometric distribution test was carried out. The annotation package GO.db 3.2.2 was used together with GOstats 2.36.0 (gene ontology analysis), and the annotation package KEGGdb 3.2.2 was used together with KEGGprofile 1.12.0 (KEGG pathway analysis).

CTL Priming Assay and Cytotoxicity Assay

From the same donor as the donor used for the establishment of the b3a2-specific T cell clone (SK), CD8$^+$ T cells and DCs were obtained. For avoiding alloreactive response, these cells were used to induce antigen-specific CTLs. By using a CD8$^+$ T cell isolation kit (Miltenyi Biotec), negative magnetic cell sorting was carried out to isolate CD8$^+$ T cells from PBMCs. In a 96-well round-bottom plate, DCs were cultured for 3 hours in the presence or absence of b3a2 peptide, and then the original CD4$^+$ Th1 clone (SK) or re-differentiated SK was added to the culture, followed by performing culture for 5 hours. After irradiation at 30Gy, CD8$^+$ T cells were added together with WT$_{1235-243}$ peptide. On Day 7, 1 µCi of [$^3$H]-thymidine was added to each culture, and, after performing 16 hours of culture, [$^3$H]-thymidine incorporation assay was used to evaluate the proliferative response of CD8$^+$ T cells. On Day 10, the same experiment was carried out again. By staining with HLA-A*2402/WT$_{123-243}$ tetramer, the frequency of WT1 peptide-specific CTLs was determined. In the presence of autologous PBMCs irradiated at 35 Gy, the CD8$^+$ T cells obtained were restimulated with WT$_{235-243}$ peptide. Thereafter, the cells were used for a cytotoxicity assay and an in vivo experiment.

In Vivo Experiment

All in vivo animal experiments were carried out with approval by the animal experiment committee of Kyoto University. Female NOD-SCID IL2RγC$^{null}$ (NSG) mice of 6 weeks old were purchased from Charles River (Yokohama, Japan), and a mixture of K562-Luc-A24-WT1 minigene cells (1.0×10$^5$ cells) with physiological saline or with WT1-specific CTLs (1.0×10$^6$ cells) was subcutaneously (s.c.) inoculated from the left tibia after hair clipping. The mice were monitored for the tumor growth and their survival. The tumor growth was weekly monitored for 4 weeks by bioluminescence imaging, and at the same time, the tumor growth was weekly monitored by external caliper measurement until death of the mice or until the mice were euthanized when the tumor diameter exceeded 25 mm.

In Vivo Bioluminescence Imaging

To tumor-bearing mice, 200 μl of D-luciferin (15 mg/ml, VivoGlo Luciferin; Promega, Madison, Wis., USA) was injected under anesthesia with 2% inhalant isoflurane, and bioluminescence images were obtained using Living Image software 3.2 and IVIS Lumina II (Xenogen, Alameda, Calif., USA).

Statistical Analyses

STATA Version 13.0 (StataCorp LP, College Station, Tex., USA) was used for all statistical analyses. For comparison of a plurality of experimental groups, significance was evaluated using a Bonferroni post hoc test together with one-way analysis of variance. For comparison of two experimental groups, an unpaired t test (two-tailed) was used. For statistical analysis of the Kaplan-Meier survival curve, a log-rank (Mantel-Cox) test was used to calculate the P-value. Statistical significance was assumed at a P-value of less than 0.05, which is indicated with asterisks in the figure.

Results

Innate Lymphocyte (ILC)-Like Properties of T-lineage Cells Differentiated from CD4$^+$ Th1 Clone-Derived iPSCs Using a T-cell regeneration protocol (FIG. 1, Panel A), CD3$^+$CD45$^+$CD5$^{dim+}$CD7$^+$CD8α$^{dim+}$CD8β$^-$ cells were obtained from iPSCs derived from the CD4$^+$ Th1 clone (SK) (left panel in FIG. 1, Panel B). These cells showed no expression of CD4 throughout the cell treatment period, and showed heterogeneous expression of several ILC markers including CD56, CD161, NKG2D, c-Kit, NKp30, NKp44, NKp46, and DNAM-1 (FIG. 1, Panel B, right panel). In spite of the heterogeneous expression of these ILC markers, the cells consistently expressed the same TCRs as those of the original CD4$^+$ Th1 clone (SK) (FIG. 1, Panel C). The iPS-T cells were divided into four subpopulations based on expression of CD161 and c-Kit, and global RNA expression of each subpopulation was compared with those of NK cells, type 1 ILCs (TLC's), type 2 ILCs (ILC2s), type 3 ILCs (ILC3s), αβ-T cells, and γδ-T cells isolated from peripheral blood. As a result, the iPS-T cells were found to have genetic properties consistent with those of the TLC1s, the NK cells, and the γδ-T cells rather than with the peripheral αβ-T cells (not shown in the figures). Expression of genes related to the ILC function in T cells and iPS-T cells was the same as their expression in the NK cells or the ILC1s (FIG. 1, Panel D). By the gene ontology analysis and the KEGG pathway analysis, enrichment of genes related to "NK cell-related cytotoxicity" in the iPS-T cells, the NK cells, and the ILC1s was revealed (not shown in the figures). Compared to the αβ-T cells, all subpopulations of the iPS-T cells showed relatively low levels of expression of BCL11B, which is an essential transcription factor for T cell differentiation, but relatively high levels of expression of ID2 and PLZF, which are transcription factors for ILCs (not shown in the figures).

Each subpopulation showed expression of type 1, type 2, and type 3 ILC-related genes in an integrated manner. All subpopulations commonly expressed ILC1-related genes such as NCAM1, NCR1, NCR2, ICOS, and IL12RB, but showed low levels of expression of IL7RA and IL1R, which are expressed on all ILCs except NK cells (FIG. 1, Panel E). TCR-independent NK cell-like cytotoxicity was found in the iPS-T cells (not shown in the figures). Similarly to the original CD4$^+$ Th1 clone (SK), the iPS-T cells showed production of IFN-γ at a high level, production of IL-4 at a relatively low level, and no production of IL-17 (FIG. 1, Panel F). Further, two times of stimulation with phytohemagglutinin (PHA)-P enables up to several thousand-fold expansion of the iPS-T cells (not shown in the figures). These data suggest that iPS-T cells produced from the CD4$^+$ Th1 clone have group 1 ILC-like properties in spite of TCR expression on those cells.

CD4 Introduction Enhances b3a2-specific Response in iPSC-Derived T Cells

During T cell activation by the HLA class II/peptide complex, binding of CD4 to HLA class II promotes TCR signaling 30- to 300-fold. It is therefore thought that CD4 is essential for complete activation of Th cells. Since the iPS-T cells expressed HLA class II-restricted TCRs as the original CD4$^+$ Th1 clone (SK) did, the inventors hypothesized that transduction of the CD4 gene in the iPS-T cells may lead to enhancement of helper T cell responses by peptide stimulation. Thus, the iPS-T cells were stimulated with PHA and when the proliferation reached the maximum, the CD4 gene was transduced with the retrovirus vector pDON-AI2 (Takara Bio) (FIG. 2, Panel A).

Figure 2:
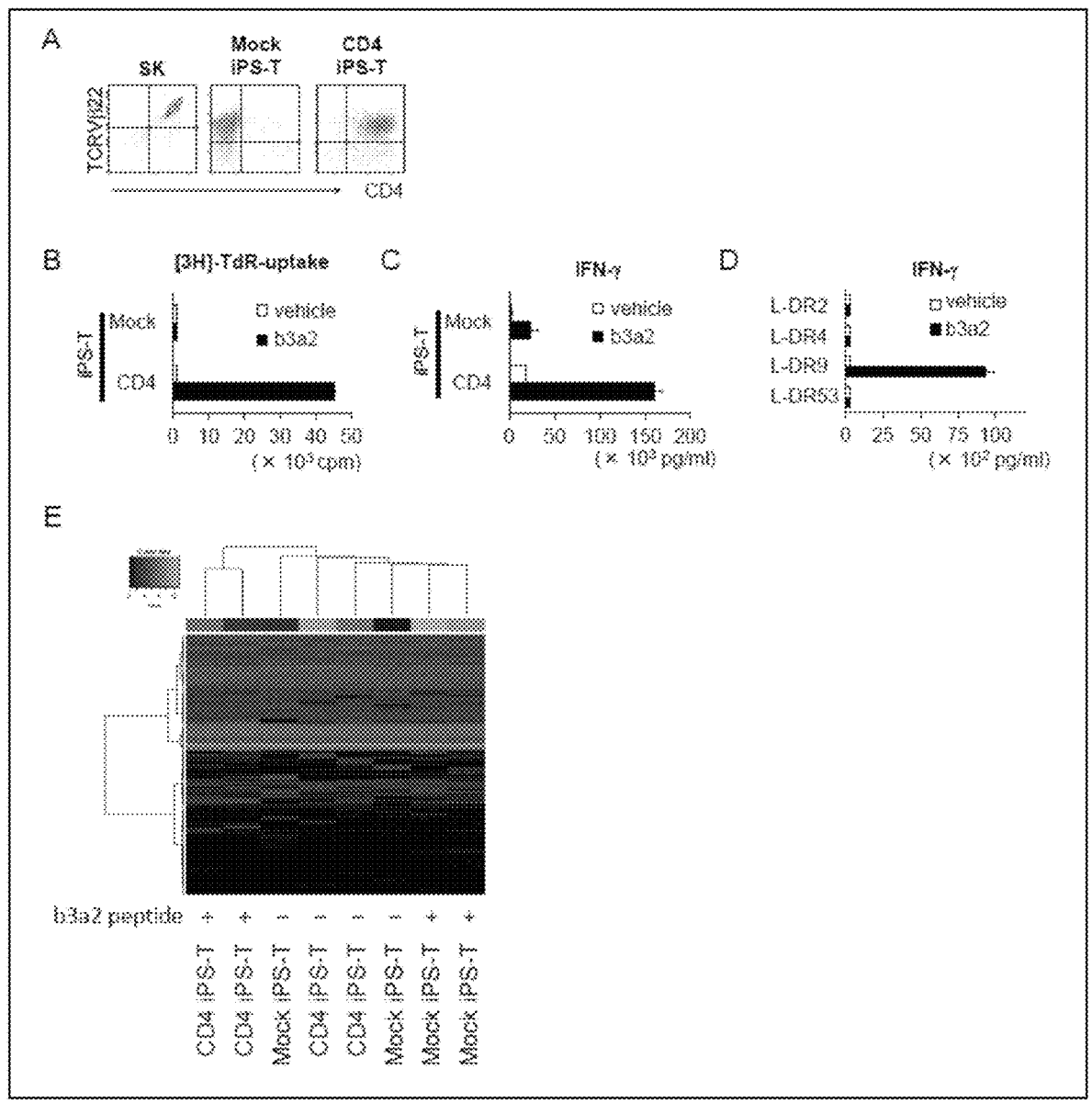
FIG. 2 is a diagram illustrating the effect of introduction of CD4 in iPS-T cells. (A) Representative flow cytometry profiles of expression of CD4 and TCR-Vb22 in the original CD4+ Th1 clone (SK), Mock-transduced iPS-T cells (Mock iPS-T cells), and CD4-transduced iPS-T cells (CD4+ iPS-T cells). (B) Proliferative responses of the Mock iPS-T cells and the CD4+ iPS-T cells to an antigen peptide. The T cells were co-cultured with autologous PBMCs in the presence of b3a2 peptide (10 µM). Proliferation was measured using [$^3$H]-thymidine incorporation assay. The data shown are averages, and represent results of three combinations of three independent experiments. (C) b3a2-peptide-specific IFN-γ production by the Mock iPS-T cells and the CD4+ iPS-T cells. The Mock iPS-T cells and the CD4+ iPS-T cells ($1\times10^5$ cells) were co-cultured for 24 hours with autologous DCs ($5\times10^4$ cells) prepulsed with b3a2 peptide (10 µM). (D) HLA-DR-restricted production of IFN-γ by the CD4+ iPS-T cells. L cell transfectants ($4\times10^4$ cells) prepulsed with b3a2 peptide (10 µM) and irradiated, expressing each HLA-DR were co-cultured with CD4+ iPS-T cells ($5\times10^4$ cells). (C, D) IFN-γ in the culture supernatant (Hour 24) was measured by ELISA. Each of the data shown is expressed as the average±SD for three culture products, and the data represent results of three combinations of three independent experiments. (E) Two-way clustering showing global gene expression profiles (halftone image). The Mock iPS-T cells and the CD4+ iPS-T cells were stimulated with a vehicle or b3a2 peptide. THP-1-expressing HLA-DR9 was used as antigen-presenting cells (APCs).

The CD4-transduced iPS-T cells (CD4$^+$ iPS-T cells) showed an antigen-dependent proliferative response and HLA-DR9-restricted cytokine production (FIG. 2, Panels B to D). The antigen specificity and the HLA class II restriction of the CD4$^+$ iPS-T cells were consistent with those of the original CD4$^+$ Th1 clone (SK) (not shown in the figure). In contrast, iPS-T cells without transduction of CD4 (Mock iPS-T cells) showed decreases in proliferation and in production of IFN-γ (FIG. 2, Panels B, and C). The effect of the CD4 transduction was found also in iPS-T cells derived from an HLA-DR53-restricted GAD65$_{113-131}$ peptide-specific CD4$^+$ Th clone (SA32.5) (not shown in the figures). Subsequently, global gene expression profiles of Mock iPS-T cells and CD4$^+$ iPS-T cells stimulated with THP-1-DR9 cells loaded with b3a2 peptide or a vehicle were analyzed. The gene expression profile of the CD4$^+$ iPS-T cells stimulated with b3a2 peptide was distinct from the gene expression profiles of the cells without stimulation by b3a2 peptide and/or without CD4 transduction (FIG. 2, Panel E). According to gene ontology analysis, it became clear that b3a2-stimulated CD4$^+$ iPS-T cells show remarkably increased expression in the cell proliferation category compared to b3a2-stimulated Mock iPS-T cells (not shown in the figures). These data indicate that transduction of the CD4 gene gives iPS-T cells an enhanced ability to produce a b3a2 peptide-specific response and an HLA class II-restricted response.

Figure 3:
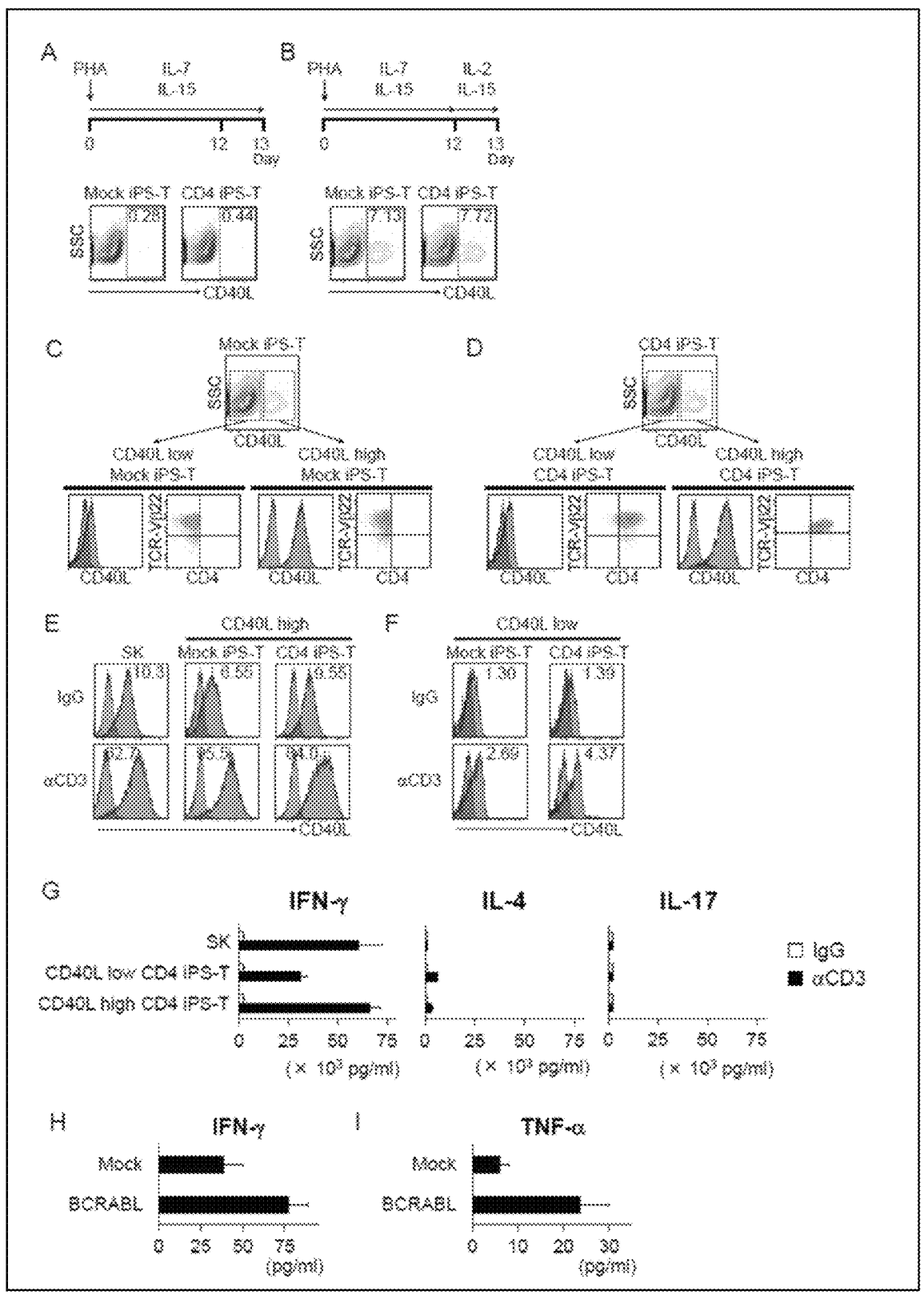
FIG. 3 is a diagram illustrating results on identification of a CD40L$^{high}$ population in iPS-T cells showing high responsiveness to TCR stimulation. (A, B) CD40L expression of the iPS-T cells observed 13 days after PHA-P stimulation. Mock iPS-T cells or CD4+ iPS-T cells were stimulated with PHA-P, and cultured in the presence of each cytokine. The upper right corner of each panel shows the frequency of CD40L-positive cells. (C, D) Expression of CD40L, CD4, and TCR-Vb22 in these subpopulations is shown. A CD40L$^{high}$ population and a CD40L$^{low}$ population after culturing in a medium containing IL-2 and IL-15 were separated by flow cytometric sorting from the Mock iPS-T cells and the CD4+ iPS-T cells, and expanded by PHA-P stimulation. (E, F) Surface expression of CD40L in different subpopulations stimulated with plate-bound control IgG or anti-CD3 monoclonal antibody (10 µg/ml). The original CD4+ Th1 clone (SK) was used as a control. The upper right corner of each panel shows the relative fluorescence intensity (RFI). (C to F) Results for CD40L (red) and isotype-matched controls (gray) are shown. (G) Cytokine production by the indicated populations stimulated with plate-bound control IgG or anti-CD3 monoclonal antibody (10 µg/ml). The original CD4+ Th1 clone (SK) was used as a control. (H, I) Cytokine production by CD40L$^{high}$ CD4+ iPS-T cells ($1\times10^5$ cells) co-cultured with THP1 cells ($5\times10^4$ cells) expressing the HLA-DR9 gene and the BCR-ABL p210 gene. (G to I) The indicated cytokines in the culture supernatant (Hour 24) were measured by a bead-based multiplex immunoassay. Each of the data shown is expressed as the average±SD for triplicate cultures, and the data represent results of three combinations of three independent experiments.

Identification of CD40L$^{high}$ Population That Efficiently Exerts T Helper (Th) Function Expression of CD40L on activated CD4$^+$ Th cells is important for maturation of DCs, and mature DCs provide costimulatory signals for effective activation and enhanced survival of antigen-specific CD8$^+$ T cells. The present inventors hypothesized that expression of CD40L by iPS-T cells may occur under stimulation by the IL-2 receptor subunit γ (common γ chain), which forms a pair with a ligand (IL-2, IL-4, IL-7, IL-9, IL-15, IL-21)-specific receptor. As a result of culturing iPS-T cells with several combinations of common γ chain cytokines, it was discovered that CD40 L expression increases under conditions with the combination of IL-2 (added at a concentration of 100 IU/ml) and IL-15 (added at a concentration of 5 ng/ml) (FIG. 3, Panels A, and B).

The IL-2/15-induced $CD40L^{high}$ population and $CD40L^{low}$ population were separated, and expanded by stimulation with phytohemagglutinin (PHA)-P. Each of the $CD40L^{high}$ population and the $CD40L^{low}$ population derived from Mock iPS-T cells or CD4$^+$ iPS-T cells expressed TCR-Vb22 in the presence of IL-2 and IL-15, and the CD40L expression levels in these populations were maintained (FIG. 3, Panels C, and D). Stimulation with an anti-CD3 antibody resulted in increased expression of CD40L only in the $CD40L^{high}$ iPS-T cells (FIG. 3, Panels E, and F). Although production of IFN-γ and TNF-α occurred at higher levels in the $CD40L^{high}$ CD4$^+$ iPS-T cells than in the $CD40L^{low}$ CD4$^+$ iPS-T cells, these two populations showed low levels of production of IL-2, IL-4, IL-6, IL-10, and IL-17 (FIG. 3, Panel G).

Upon stimulation with DCs loaded with b3a2 peptide, co-expression of CD4 and CD40L occurred to cause synergistic enhancement of production of IFN-γ and TNF-α, showing a cumulative Th1-biased cytokine profile (not shown in the figures). Further, when $CD40L^{high}$ CD4$^+$ iPS-T cells were co-cultured with THP-1-DR9 cells expressing BCR-ABL p210 protein, the iPS-T cells produced IFN-γ and TNF-α, indicating their ability to respond to the naturally processed BCR-ABL p210 epitope (FIG. 3, Panels H, and I). Further, $CD40L^{high}$ CD4$^+$ iPS-T cells have an ability to expand in response to repetitive stimulation, without affecting CD3 expression, $CD5^{dim}$ expression, CD7 expression, and CD8a expression (not shown in the figures). Similar findings related to CD40L expression were obtained for iPS-T cells derived from the HLA-DR53-restricted $GAD65_{113-131}$ peptide-specific CD4$^+$ Th clone (SA32.5) (not shown in the figures). In summary, a CD4$^+$ iPS-T cell population which is capable of increasing CD40L expression by TCR stimulation, and which has an excellent ability to respond to stimulation with an antigen peptide, was identified.

Figure 4:
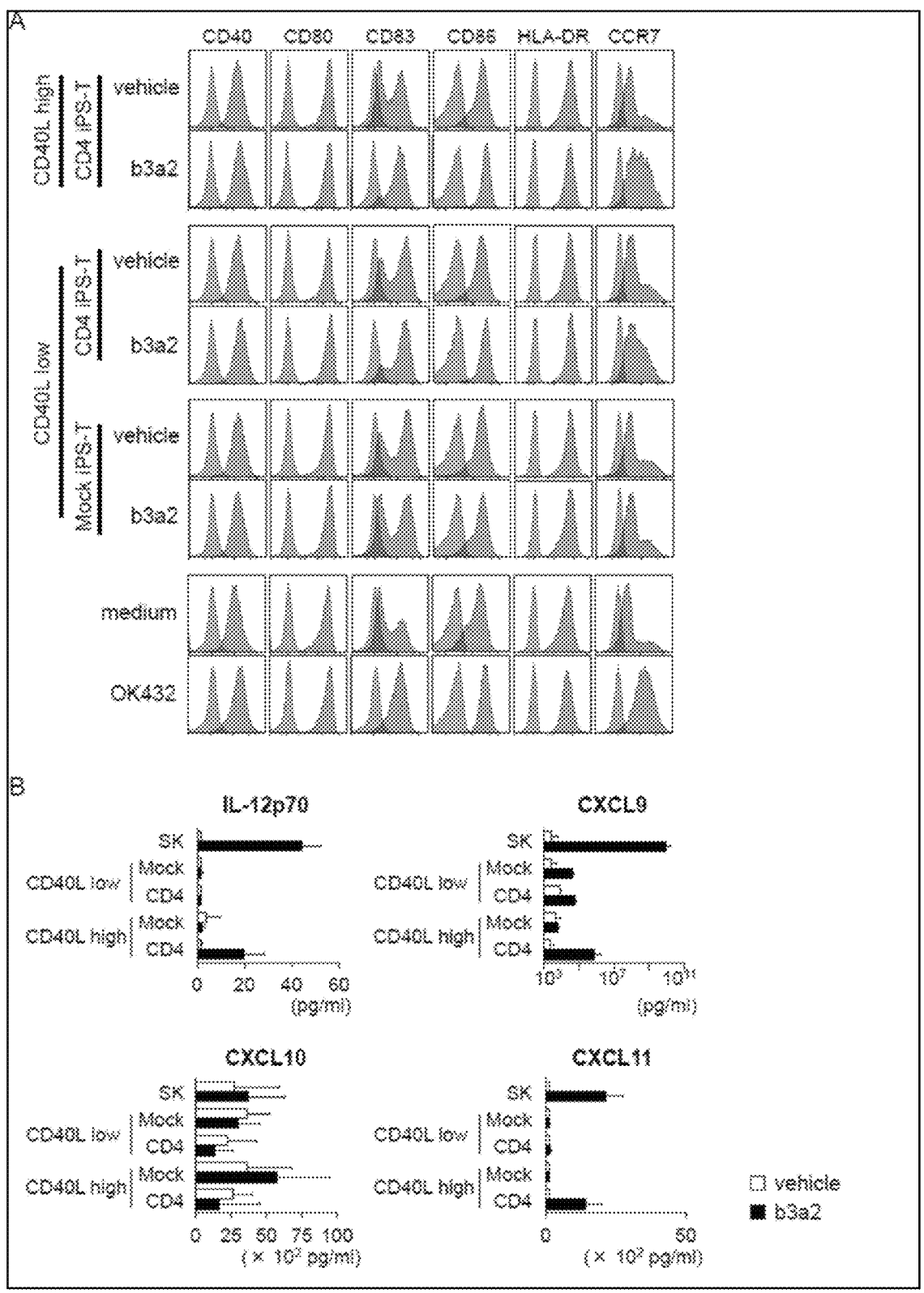
FIG. 4 is a diagram illustrating results of DC activation by CD40L$^{high}$ CD4$^+$ iPS-T cells. (A) Representative flow cytometry profiles of molecules on DCs. DCs pulsed with a vehicle or b3a2 peptide were cultured for 24 hours with each kind of CD4$^+$ iPS-T cells at a ratio of DCs/CD4$^+$ iPS-T cells of 5:1. OK432 (10 µg/ml) maturation-treated DCs and medium control DCs were used as controls. Results for surface molecules (red) and isotype-matched controls (gray) are shown. (B) Cytokine production by DCs co-cultured with each kind of CD4$^+$ iPS-T cells. Cytokines in the culture supernatant were measured by a bead-based multiplex immunoassay. Each kind of CD4$^+$ iPS-T cells (1×10$^4$ cells) were co-cultured for 24 hours with autologous DCs (2.5×10$^4$ cells) prepulsed with b3a2 peptide (10 µM). The original CD4$^+$ Th1 clone (SK) was used as a control. Each of the data shown is expressed as the average±SD for triplicate cultures, and the data represent results of three combinations of three independent experiments.

Subsequently, analysis of the cellular adjuvant function of CD4$^+$ iPS-T cells to induce DC maturation was carried out. When $CD40L^{high}$ CD4$^+$ iPS-T cells were co-cultured with immature DCs prepulsed with b3a2 peptide, the iPS-T cells induced complete maturation of DCs, which maturation was equivalent to OK432-induced maturation (FIG. 4, Panel A). In contrast, DC maturation with $CD40L^{low}$ CD4$^+$ iPS-T cells did not function (FIG. 4, Panel A). Furthermore, $CD40L^{low}$ Mock iPS-T cells failed to induce DC maturation, possibly due to impaired recognition of the HLA class II/peptide complex due to the absence of CD4 (FIG. 4, Panel A). $CD40L^{high}$ CD4$^+$ iPS-T cells also enhanced the production of IL-12p70, CXCL9, and CXCL11, which are important soluble factors for activation and migration of NK cells, Th cells, and CTLs (FIG. 4, Panel B). These data indicate that $CD40L^{high}$ CD4$^+$ iPS-T cells have an excellent ability to induce DC maturation.

$CD40L^{high}$CD4$^+$ iPSC-Derived T Cell Reduced TCR-Independent Cytotoxicity

Figure 5:
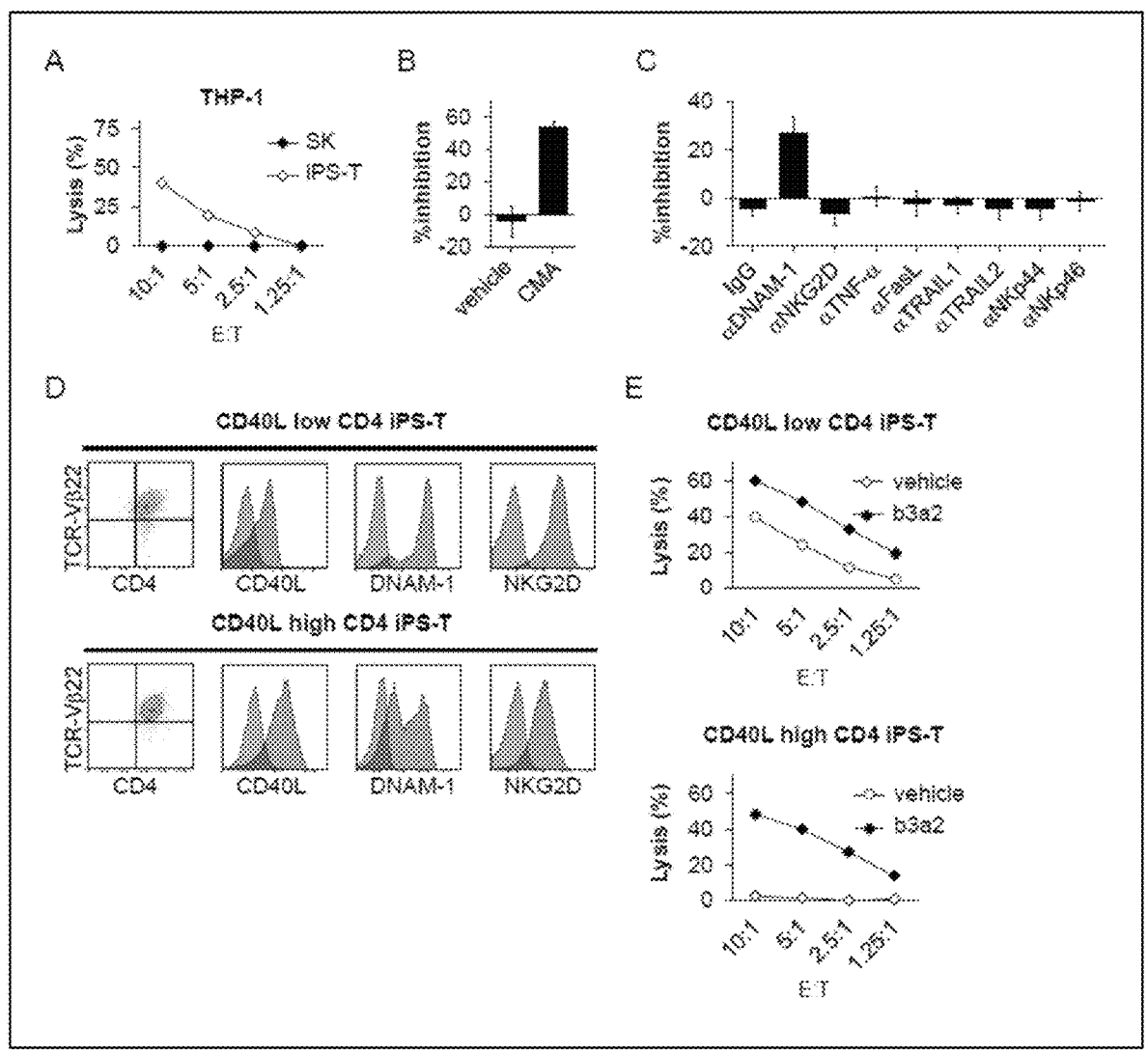
FIG. 5 is a diagram illustrating results of analysis of cytotoxicity of CD40L$^{high}$ CD4$^+$ iPS-T cells. (A) Cytotoxic activity of the iPS-T cells against THP-1 cells. (B, C) Cytotoxicity of the iPS-T cells against THP-1 cells at an effector/target (E: T) ratio of 2.5:1. (B) Mock iPS-T cells were treated with 10 nM concanamycin A (CMA), which blocks perforin. (C) Antibodies that inhibit receptor-ligand interaction were added. (D) Representative flow cytometry profiles of TCR-Vb22, CD4, CD40L, DNAM-1, and NKG2D in each kind of CD4$^+$ iPS-T cells. (E) Cytotoxic activity of each kind of CD4$^+$ iPS-T cells against HLA-DR9-expressing THP-1 cells loaded with a vehicle or b3a2 peptide (5 µM). (A to C, E) Cytotoxicity was measured by $^{51}$Cr release assay for 4 hours at the indicated E:T ratios. The data shown represent results of three combinations of three independent experiments.

CD4$^+$ Th1 clone (SK)-derived iPS-T cells showed antigen-independent cytotoxicity against the THP-1 line (FIG. 5, Panel A). The cytotoxicity against the THP-1 line was partially dependent on perforin and DNAM-1 (FIG. 5, Panels B, and C). $CD40L^{high}$ CD4$^+$ iPS-T cells conditioned by IL-2/IL-15 exhibited reduced expression of DNAM-1 and NKG2D compared with $CD40L^{low}$ CD4$^+$ iPS-T cells (FIG. 5, Panel D). Consistent with the reduced expression of DNAM-1 and NKG2D, $CD40L^{high}$ CD4$^+$ iPS-T cells reduced NK cell-like cytotoxicity against THP-1-DR9 cells while retaining b3a2-specific cytotoxicity (FIG. 5, Panel E). These data indicate that the $CD40L^{high}$ CD4$^+$ iPS-T cells reduced antigen-independent cytotoxicity by reducing expression of DNAM-1.

Figure 6:
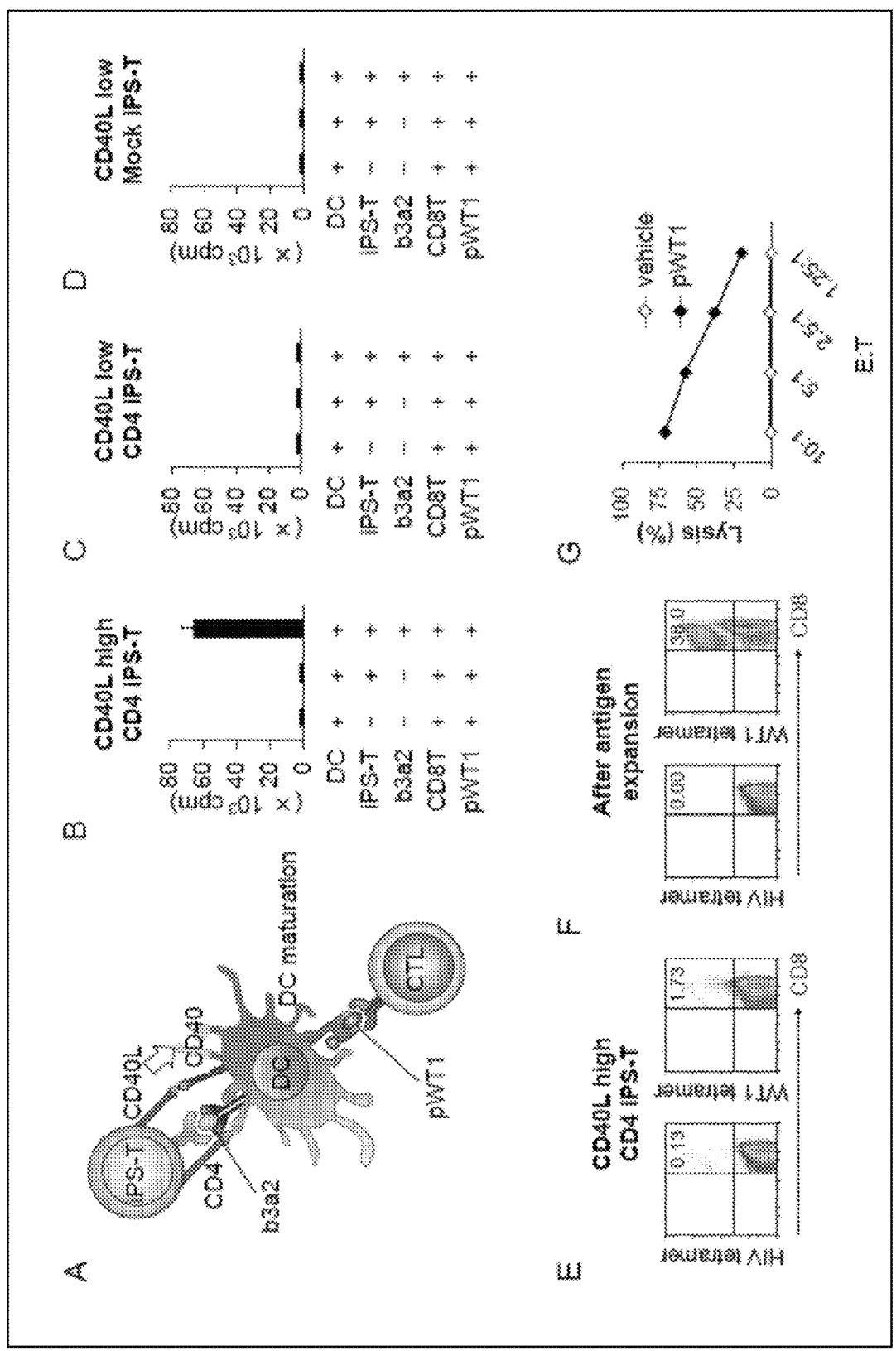
FIG. 6 is a diagram illustrating results of analysis of the mechanism of induction of leukemia antigen-specific CTLs by CD40L$^{high}$ CD4$^+$ iPS-T cells. (A) Mechanism of WT1-specific CTL priming. pWT1 represents WT1 peptide, and b3a2 represents b3a2 peptide. When b3a2 peptide presented by a DC is recognized by an iPS-T cell, the activated iPS-T cell increases expression of CD40L. DC maturation is induced by CD40 ligation by CD40L. Activation of the WT1 peptide-specific CTL is promoted by increased expression of costimulatory molecules and increased production of cytokines by the DC. (B to D) Proliferative response of CD8$^+$ T cells. Each kind of the iPS-T cells (5×10$^3$ cells) and DCs (1×10$^4$ cells) were first co-cultured with b3a2 peptide (5 µM) or without b3a2 peptide for 5 hours to allow maturation of the DCs, and then the DCs and the iPS-T cells were irradiated, followed by culturing with autologous CD8$^+$ T cells (5×10$^4$ cells) in the presence of WT1 peptide (5 µM). The proliferative response (Day 7) was measured as the amount of [$^3$H]-thymidine incorporated. Each of the data shown is expressed as the average±SD for triplicate cultures, and the data represent results of three combinations of three independent experiments. (E) Frequency of WT1/HLA-A24 tetramer-positive CD8$^+$ T cells primed by CD40L$^{high}$ CD4$^+$ iPS-T cell-conditioned DCs. CD40L$^{high}$ CD4$^+$ iPS-T cells (5×10$^3$ cells) and DCs (1×10$^4$ cells) prepulsed with b3a2 peptide (5 µM) were first co-cultured for 5 hours to allow maturation of the DCs, and then the DCs and the CD4$^+$ iPS-T cells were irradiated, followed by and culturing with autologous CD8$^+$ T cells (5×10$^4$ cells) in the presence of WT1 peptide (5 µM). Results of tetramer staining on Day 10 after the stimulation are shown. (F) Frequency of WT1/HLA-A24 tetramer-positive CD8$^+$ T cells after three times of stimulation with WT1 peptide. (E, F) Representative flow cytometry profiles from three independent experiments. HIV-env/HLA-A24 tetramer was used as a control. (G) Cytotoxic activities of expanded WT1-specific CD8$^+$ T cells against K562-A24 cells loaded with a vehicle or WT1 peptide. Cytotoxicity was measured by $^{51}$Cr release assay for 4 hours at the indicated effector/target (E: T) ratios. The data represent results of three combinations of three independent experiments.

$CD40L^{high}$ CD4$^+$ iPSC-derived T Cells Efficiently Induce Primary Expansion of Leukemia Antigen-Specific CTLs CD4$^+$ Th cells assist priming of HLA class I-restricted CD8$^+$ CTLs through DC activation. In order to determine whether $CD40L^{high}$ CD4$^+$ iPS-T cells have an ability to induce a leukemia antigen-specific CTL response, DCs loaded with a solvent alone or with b3a2 peptide were cultured with $CD40L^{high}$ CD4$^+$ iPS-T cells, and the conditioned DCs were loaded with $WT1_{235-243}$ peptide, followed by irradiation and then culturing with CD8$^+$ T cells (FIG. 6, Panel A). After 7 days of culture, proliferation of the CD8$^+$ T cells was evaluated. When a co-culture product of $CD40L^{high}$ CD4$^+$ iPS-T cells/b3a2 peptide-conditioned DCs was used as APCs, markedly enhanced proliferation of CD8$^+$ T cells was found upon stimulation with $WT1_{235-243}$ peptide (FIG. 6, Panel B). In contrast, neither a co-culture product of $CD40L^{low}$ CD4$^+$ iPS-T cells/b3a2-conditioned DCs nor a co-cultured product of $CD40L^{low}$ Mock iPS-T cells/b3a2-conditioned DCs induced proliferation of CD8$^+$ T cells (FIG. 6, Panels C, and D). The CTLs stimulated by the co-culture product of $CD40L^{high}$ CD4$^+$ iPS-T cells/b3a2 peptide-conditioned DCs contained WT1-tetramer-positive T cells at a high frequency (FIG. 6, Panel E). WT1 peptide-specific CTLs were further expanded by stimulation with WT1 peptide, which stimulation was repeated three times (FIG. 6, Panel F). The expanded WT1-specific CTLs showed cytotoxic activity against HLA-A24-expressing K562 cells loaded with WT1 peptide, but did not show cytotoxic activity against cells loaded with a solvent alone (FIG. 6, Panel G). These data indicate that activation of $CD40L^{high}$ CD4$^+$ iPS-T cells, which exert cellular adjuvant properties, by b3a2 peptide enables enhancement of leukemia antigen-specific CTL responses through DC activation. This is consistent with the T helper function of the original CD4$^+$ Th1 clone (SK) (not shown in the figures).

Figure 7:
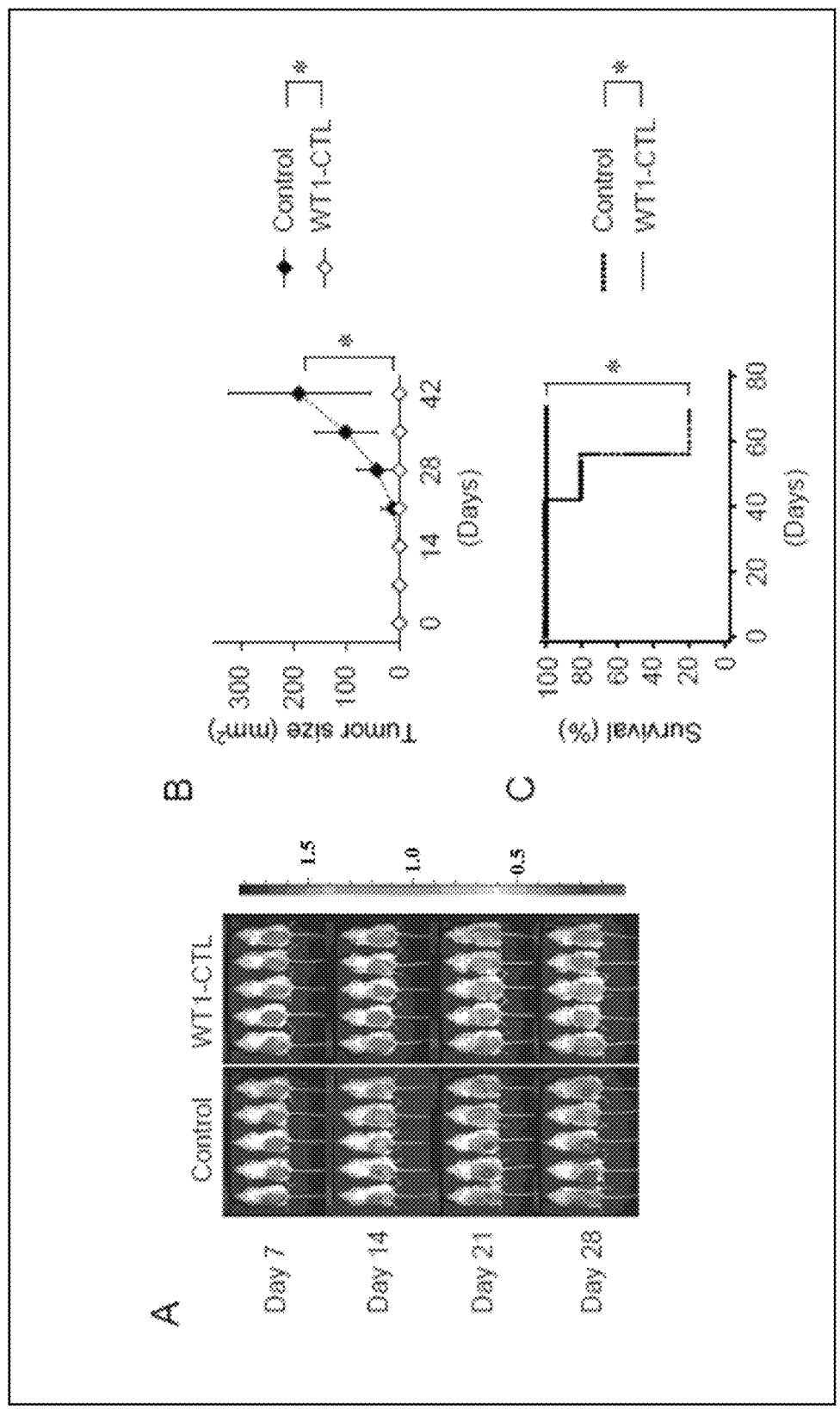
FIG. 7 is a diagram illustrating antileukemic activity of CTLs (WT1-specific CTLs) primed by CD40L$^{high}$ CD4$^+$ iPS-T cell-conditioned DCs. (A) In vivo anti-leukemic action (photographs). A mixture of K562-A24-Luc-WT1 minigene cells with physiological saline or with WT1-specific CTLs was subcutaneously injected to NSG mice. Tumor burden was measured weekly by bioluminescence imaging. (B) The average tumor sizes from Day 0 to Day 42 are shown for each group. Each error bar represents±SD. "*" represents a P value of less than 0.05 according to unpaired Student's t test (two-tailed). (C) Kaplan-Meier survival curves for treated mice and control mice. "*" represents a P value of less than 0.05 according to the log rank (Mantel-Cox) test. (WT1-CTL-treated, n=10; untreated, n=5).

WT1-Specific CTLs Stimulated by Interaction of $CD40L^{high}$ CD4$^+$ iPSC-Derived T Cells with DCs Exert Anti-leukemic Action In Vivo In order to investigate whether primed WT1 peptide-specific CTLs exert an anti-leukemic action in vivo, WT1 epitope-expressing K562 cells were subcutaneously injected into NSG mice with or without WT1 peptide-specific CTLs. Tumor growth was weekly monitored by bioluminescence imaging and external caliper measurement. In the presence of WT1 peptide-specific CTLs, tumor growth was markedly suppressed (FIG. 7, Panels A, and B) and the mice exhibited marked prolongation of survival (FIG. 7, Panel C). Leukemic antigen-specific CTLs stimulated by the interaction of $CD40L^{high}$ CD4$^+$ iPS-T cells with DCs can exert an effective anti-leukemic action.

What is claimed is:

1. A method of producing helper T cells comprising:
   (i) culturing T cells, which have been induced from pluripotent stem cells and into which a CD4 gene or a gene product thereof has been introduced, in a medium containing IL-2 and IL-15; and
   (ii) isolating CD40L-highly expressing T cells from cells obtained in Step (i).

2. The method according to claim 1, wherein the concentration of the IL-2 is 10 to 500 IU/ml, and the concentration of the IL-15 is 1 to 50 ng/ml.

3. The method according to claim 1, wherein the T cells have been induced from the pluripotent stem cells by a method comprising:

(1) inducing CD34-positive hematopoietic progenitor cells from pluripotent stem cells; and
   (2) culturing CD34-positive hematopoietic progenitor cells obtained in Step (1), in the presence of FLT3L and IL-7.

4. The method according to claim 3, wherein Step (1) comprises co-culturing pluripotent stem cells with C3H10T1/2, followed by co-culturing with C3H10T1/2 in the presence of VEGF, FLT3L, and SCF.

5. The method according to claim 3, wherein Step (2) comprises co-culturing the CD34-positive hematopoietic progenitor cells with stromal cells.

6. The method according to claim 3, wherein said method of inducing the T cells from the pluripotent stem cells further comprises:

(3) co-culturing cells obtained in Step (2), with peripheral blood mononuclear cells in the presence of IL-7 and IL-15.

7. The method according to claim 3, wherein said method of inducing T cells from the pluripotent stem cells further comprises:
bringing cells obtained in Step (2) into contact with mitogen, and/or
bringing cells obtained in Step (3) into contact with mitogen.

8. The method according to claim 1, wherein the CD4 gene has been introduced using a retrovirus vector.

9. The method according to claim 1, wherein the pluripotent stem cells are pluripotent stem cells having a rearranged TCR sequence of interest.

10. The method according to claim 9, wherein the pluripotent stem cells are human iPS cells induced from lymphocytes that recognize a desired antigen(s).

11. The method according to claim 10, wherein the lymphocytes that recognize a desired antigen(s) are lymphocytes that recognize BCR/ABL.

\* \* \* \* \*